US012303279B2

(12) United States Patent
Jeong et al.

(10) Patent No.: US 12,303,279 B2
(45) Date of Patent: May 20, 2025

(54) ELECTROCARDIOGRAM DATA PROCESSING SERVER, METHOD AND COMPUTER PROGRAM FOR DISPLAYING ANALYSIS DATA OF ELECTROCARDIOGRAM SIGNAL

(71) Applicant: ATSENS CO., LTD., Gyeonggi-do (KR)

(72) Inventors: Jong Ook Jeong, Gyeonggi-do (KR); Chang Ho Lee, Gyeonggi-do (KR); Kab Mun Cha, Gyeonggi-do (KR); Jin A Lee, Gyeonggi-do (KR)

(73) Assignee: ATsens Co., Ltd., Gyeonggi-do (KR)

( * ) Notice: Subject to any disclaimer, the term of this patent is extended or adjusted under 35 U.S.C. 154(b) by 250 days.

(21) Appl. No.: 17/888,592

(22) Filed: Aug. 16, 2022

(65) Prior Publication Data

US 2023/0117220 A1 Apr. 20, 2023

(30) Foreign Application Priority Data

Oct. 18, 2021 (KR) .......................... 10-2021-0138599

(51) Int. Cl.
*A61B 5/339* (2021.01)
*A61B 5/00* (2006.01)
*A61B 5/346* (2021.01)

(52) U.S. Cl.
CPC ............ *A61B 5/339* (2021.01); *A61B 5/0006* (2013.01); *A61B 5/346* (2021.01)

(58) Field of Classification Search
CPC ..... A61B 5/0006; A61B 5/0022; A61B 5/339; A61B 5/346; A61B 5/7264
See application file for complete search history.

(56) References Cited

U.S. PATENT DOCUMENTS

2017/0011210 A1* 1/2017 Cheong ................. A61B 5/681

FOREIGN PATENT DOCUMENTS

| JP | 2005095469 A | 4/2005 |
|---|---|---|
| JP | 2017148364 A | 8/2017 |
| KR | 1020120113985 A | 10/2012 |
| KR | 1020200004722 A | 1/2020 |
| KR | 102134206 B1 | 7/2020 |

(Continued)

OTHER PUBLICATIONS

Notice of Allowance issued to corresponding Korean Application No. 10-2021-0138599, issued Apr. 25, 2022, 2 pages.

(Continued)

*Primary Examiner* — George Manuel
(74) *Attorney, Agent, or Firm* — Guntin & Gust, PLC; Miyoung Shin

(57) ABSTRACT

A method of displaying analysis data of an electrocardiogram signal includes receiving, by an electrocardiogram data processing server, a load input with respect to a first electrocardiogram signal from a user terminal, generating, by the electrocardiogram data processing server, data including analysis data of the first electrocardiogram signal and a first expected analysis time of the first electrocardiogram signal, and transmitting, by the electrocardiogram data processing server, the analysis data to the user terminal to display, on the user terminal, a first window displaying the first electrocardiogram signal and a second window displaying the first expected analysis time.

7 Claims, 19 Drawing Sheets

(56) References Cited

FOREIGN PATENT DOCUMENTS

| | | |
|---|---|---|
| KR | 1020200109233 A | 9/2020 |
| WO | 2020184926 A1 | 9/2020 |
| WO | 2021132933 A1 | 7/2021 |

OTHER PUBLICATIONS

Office Action issued in corresponding Korean Application No. No. 10-2021-0138599, issued Dec. 21, 2021, 5 pages.

* cited by examiner

FIG. 15

| LABEL_P | DAY | START | DURATION | END |
|---|---|---|---|---|
| AFIB_1 | 1 | 4:00:00 | 0:00:35 | 4:00:35 |
| AFIB_1 | 3 | 8:00:00 | 0:11:00 | 8:11:00 |
| AFIB_1 | 3 | 8:15:00 | 0:08:40 | 8:23:40 |
| AFIB_1 | 3 | 8:24:00 | 0:08:10 | 8:32:10 |
| AFIB_1 | 3 | 8:35:00 | 0:05:33 | 8:40:33 |
| AFIB_1 | 3 | 8:43:30 | 0:07:50 | 8:51:20 |
| AFIB_1 | 3 | 10:10:00 | 0:00:12 | 10:10:12 |
| AFIB_1 | 3 | 13:10:00 | 0:07:10 | 13:17:10 |
| AFIB_1 | 3 | 13:30:00 | 0:05:40 | 13:35:40 |
| AFIB_1 | 3 | 13:38:00 | 0:07:55 | 13:45:55 |
| AFIB_1 | 3 | 13:45:00 | 0:05:31 | 13:50:31 |
| AFIB_1 | 3 | 13:55:00 | 0:05:30 | 14:00:30 |
| AFIB_1 | 3 | 15:15:00 | 0:00:40 | 15:15:40 |
| AFIB_1 | 3 | 23:01:00 | 0:00:27 | 23:01:27 |
| AFIB_1 | 3 | 23:10:00 | 0:00:25 | 23:10:25 |
| AFIB_1 | 5 | 7:45:00 | 0:10:30 | 7:55:30 |
| AFIB_1 | 5 | 7:58:00 | 0:08:30 | 8:06:30 |
| AFIB_1 | 5 | 8:08:20 | 0:06:55 | 8:15:15 |
| AFIB_1 | 5 | 8:17:00 | 0:06:49 | 8:23:49 |
| AFIB_1 | 5 | 8:25:10 | 0:06:34 | 8:31:44 |
| AFIB_1 | 5 | 12:55:00 | 0:08:10 | 13:03:10 |
| AFIB_1 | 5 | 13:05:00 | 0:07:40 | 13:12:40 |
| AFIB_1 | 5 | 13:14:00 | 0:07:30 | 13:21:30 |
| AFIB_1 | 5 | 13:22:00 | 0:07:28 | 13:29:28 |
| AFIB_1 | 5 | 13:32:00 | 0:07:10 | 13:37:10 |
| AFIB_2 | 7 | 8:10:00 | 0:01:10 | 8:11:10 |
| AFIB_2 | 7 | 8:11:00 | 0:00:15 | 8:11:15 |
| AFIB_2 | 7 | 8:13:00 | 0:00:08 | 8:13:08 |
| AFIB_2 | 9 | 8:00:00 | 0:00:10 | 8:00:10 |
| AFIB_1 | 11 | 8:11:00 | 0:09:40 | 8:20:40 |
| AFIB_1 | 11 | 8:22:00 | 0:07:10 | 8:29:10 |

FIG. 16

| LABEL_P | FREQUENCY |
|---|---|
| AFIB_1 | 27 |
| AFIB_2 | 4 |

ELECTROCARDIOGRAM DATA PROCESSING SERVER, METHOD AND COMPUTER PROGRAM FOR DISPLAYING ANALYSIS DATA OF ELECTROCARDIOGRAM SIGNAL

CROSS-REFERENCE TO RELATED APPLICATION

This application is based on and claims priority under 35 U.S.C. § 119 to Korean Patent Application No. 10-2021-0138599, filed on Oct. 18, 2021, in the Korean Intellectual Property Office, the disclosure of which is incorporated by reference herein in its entirety.

BACKGROUND

1. Field

One or more embodiments relate to an electrocardiogram signal processing server, a method, and a computer program for displaying analysis data of the electrocardiogram signal.

2. Description of the Related Art

When the cardiac muscles contract and relax, a potential difference is generated by electrical depolarization and repolarization. Such a potential difference may be detected by attaching a surface electrode onto the surface of the skin, and the detected potential difference is referred to as an electrocardiogram. The electrocardiogram may have a level ranging from tens of microvolts (μV) to several millivolts (mV) and a frequency band less than 100 Hz.

To identify cardiac illnesses, it is required to measure the electrocardiogram for a certain time period, and a doctor may diagnose cardiac illnesses based on an analysis result of the measured electrocardiogram input by an analyst. It may take three to six hours for an analyst to analyze the electrocardiogram measured for 24 hours, and the analysis time of the electrocardiogram may increase proportional to the measurement time of the electrocardiogram.

Moreover, in some cases, it may take more or less time than expected for an analyst to actually conduct a requested analysis, which may lead to a discrepancy between analysis time calculating in payment to the analyst and actual analysis time.

Accordingly, there has been a growing need for predicting the time required for electrocardiogram analysis.

The aforementioned background art is technical information which has been owned by the inventor to derive the present disclosure or learned by the inventor in the process of deriving the present disclosure by the inventor, and thus, is not necessarily a prior art which was disclosed to the general public to general public before the filing of the present application.

SUMMARY

One or more embodiments include a method of displaying analysis data of an electrocardiogram signal.

Additional aspects will be set forth in part in the description which follows and, in part, will be apparent from the description, or may be learned by practice of the presented embodiments of the disclosure.

According to one or more embodiments, a method of displaying analysis data of an electrocardiogram signal includes: receiving, by an electrocardiogram data processing server, a load input with respect to a first electrocardiogram signal from a user terminal; generating, by the electrocardiogram data processing server, data including the first electrocardiogram signal and a first expected analysis time of the first electrocardiogram signal to the user terminal; and transmitting, by the electrocardiogram data processing server, the data to the user terminal to display, on the user terminal, a first window displaying the first electrocardiogram signal and a second window displaying the first expected analysis time.

The generating of the data may further include calculating, by the electrocardiogram data processing server, the first expected analysis time by using data of previously performed analysis of electrocardiogram signals and classification data of the first electrocardiogram signal.

The method may further include generating, by the electrocardiogram data processing server, first data regarding analysis times of electrocardiogram signals performed by a first analyst and second data regarding analysis times of electrocardiogram signals performed by a second analyst, and transmitting analysis processed data including the first data and the second data to the user terminal to display a third window displaying the analysis processed data on the user terminal.

The first data or the second data may further include expected analysis time of the first electrocardiogram signal calculated by using analysis times of the electrocardiogram signals performed by the first analyst or the second analyst or an average value of expected analysis times performed by the first analyst or the second analyst.

According to one or more embodiments, the method may further include: receiving, by the electrocardiogram data processing server, an input selecting the first analyst of the analysis processed data from the user terminal; recalculating, by the electrocardiogram data processing server, the first expected analysis time of the first electrocardiogram signal by using the first data performed by the first analyst; and transmitting, by the electrocardiogram data processing server, data regarding the first expected analysis time to the user terminal to display the recalculated first expected analysis time on the second window of the user terminal.

According to one or more embodiments, the method may further include generating first data regarding analysis times of electrocardiogram signals analyzed by a first analysis module and second data regarding analysis times of electrocardiogram signals analyzed by a second analysis module, and transmitting analysis processed data including the first data and the second data to the user terminal to display a third window displaying the analysis processed data on the user terminal.

According to one or more embodiments, the method may further include: receiving, by the electrocardiogram data processing server, an input selecting the first analysis module of the analysis processed data from the user terminal; recalculating, by the electrocardiogram data processing server, the first expected analysis time of the first electrocardiogram signal by using the first data performed by the first analysis module; and transmitting, by the electrocardiogram data processing server, data regarding the first expected analysis time to the user terminal to display the recalculated first expected analysis time on the second window of the user terminal.

The first data or the second data may further include expected analysis time of the first electrocardiogram signal calculated by using analysis times of the electrocardiogram signal performed by the first analysis module or the second analysis module.

The first window may display the analysis data of the electrocardiogram signal on a measurement day basis.

According to one or more embodiments, a method of displaying analysis data of an electrocardiogram signal includes: calculating at least one of a duration, a symptom value, and a label value with respect to each signal section of electrocardiogram signals; among calculated information, setting first information as display set information and second information excluding the first information as hidden set information; and generating output data to classify the electrocardiogram signals by the first information for display.

The setting of the first information and the second information may include displaying a plurality of duration values which are set with respect to the electrocardiogram signals on a list screen, and when an input to select a first duration value among the plurality of duration values is detected, setting the first duration value as display set information and the rest of information as hidden set information.

The setting of the first information and the second information may include displaying a plurality of symptom values which are set with respect to the electrocardiogram signals on a list screen, and when an input to select a first symptom value among the plurality of symptom values is detected, setting the first symptom value as display set information and the rest of information as hidden set information.

The setting of the first information and the second information may include displaying a plurality of specific symptoms are set with respect to the electrocardiogram signals on a list screen, and when an input to select a first specific symptom among the plurality of specific symptoms is detected, setting the first symptom as display set information and the rest of information as hidden set information.

The setting of the first information and the second information may include displaying a plurality of reference waveforms which are set with respect to the electrocardiogram signals on a list screen, and when an input to select a first reference waveform among the plurality of reference waveforms is detected, setting the first reference waveform as display set information and the rest of information as hidden set information.

According to one or more embodiments, the method may further include generating an analysis request signal for signal sections of an electrocardiogram signal included in the output data when an input complete signal for the output data is detected, and transmitting the analysis request signal to the analyst terminal.

According to one or more embodiments, the method may further include: when a report signal for the analysis request signal is received, transmitting output data according to the report signal to a medical staff terminal; and when a confirm signal for the output data is received from the medical staff terminal, changing a status of the analysis request signal to a complete status.

The first information or the second information may include data to be displayed, which is classified on a measurement day basis.

A computer program according to an embodiment may be stored by using a computer in a medium to perform any one method according to embodiments of the present disclosure.

In addition to this, other methods and systems to implement the present disclosure as well as a computer-readable recording medium for recording a computer program to execute the method may be further provided.

In addition to the foregoing, other aspects, characteristics, and advantages may be clarified by the drawings, claims, and detailed description below.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 15 is a diagram showing sections to be analyzed corresponding to analysis conditions;

FIG. 16 is a diagram showing an example of a frequency of occurrence of a first label and a second label in analysis target sections of FIG. 15;

DETAILED DESCRIPTION

Figure 1:
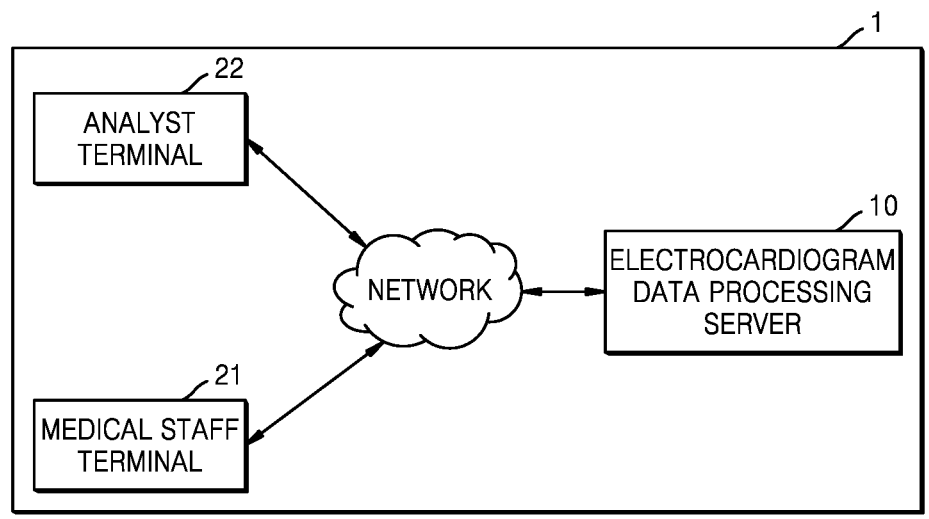
FIG. 1 is a diagram of a network environment of an electrocardiogram data processing system according to one or more embodiments.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, the components and effects of the present disclosure are described in detail with reference to embodiments illustrated in the accompanying drawings.

As the present disclosure allows for various changes and numerous embodiments, exemplary embodiments will be illustrated in the drawings and described in detail in the written description. The effects and features of the present disclosure, as well as the methods to achieve them will become apparent with reference to the below embodiments described in detail along with the drawings. However, the present disclosure may be embodied in many different forms and should not be construed as limited to the exemplary embodiments set forth herein.

Hereinafter, exemplary embodiments are described in detail with reference to the attached drawings. Like or corresponding reference numerals in the drawings denote like elements, and any redundant descriptions thereon will be omitted.

In the present specification, the terms "training," "learning," etc. are not intended to indicate the human mental operation, such as educational activities, but rather are construed as performance of machine learning through computing according to a process.

It will be understood that although the terms "first," "second," etc. may be used herein to describe various components, these components should not be limited by these terms. These components are only used to distinguish one component from another.

An expression used in the singular encompasses the expression of the plural, unless it has a clearly different meaning in the context.

It will be further understood that the terms "comprises" and/or "comprising" used herein specify the presence of stated features or components, but do not preclude the presence or addition of one or more other features or components.

Sizes of components in the drawings may be exaggerated or reduced for convenience of explanation. In other words, since sizes and thicknesses of components in the drawings are arbitrarily illustrated for convenience of explanation, the present disclosure is not limited thereto.

When a certain embodiment may be implemented differently, a specific process order may be performed differently from the described order. For example, two consecutively described processes may be performed substantially at the same time or performed in an order opposite to the described order.

According to an embodiment, a network means a connection established (or formed) by using any type of communication methods, and may refer to a communication network connected though all types of communication methods to receive and transmit data between terminals or between a terminal and a server.

The aforementioned all types of communication methods may encompass various communication methods using a certain communication standard, a certain frequency band, a certain protocol, or a certain channel. For example, the communication methods may include Bluetooth, Bluetooth low energy (BLE), Wi-Fi, Zigbee, 3G, long term evolution (LTE), and communication using ultrasonic waves, and may further include short-range communication, long-distance communication, wireless communication, and wired communication. However, the present disclosure is not limited thereto.

According to an embodiment, the short-range communication may refer to a communication method which is only available when a communication device (a terminal or a server) is within a certain range, and may include, for example Bluetooth, near field communication (NFC), etc. The long-distance communication may refer to a communication method which is available regardless of a distance from a communication device. For example, the long-distance communication may mean a method facilitating communication through a repeater, such as a Wireless Access Point (AP) even when a distance between two communication devices is greater than or equal to a certain distance, and may include communication using a cellular network (3G, LTE, etc.) such as a short message service (SMS), a telephone service, etc. However, the present disclosure is not limited thereto. When online activities are provided by using a network, the implication is that communication between a server and a terminal may be performed through any type of communication method.

FIG. 1 is a diagram of a network environment of an electrocardiogram data processing system 1 according to one or more embodiments.

Figure 11:
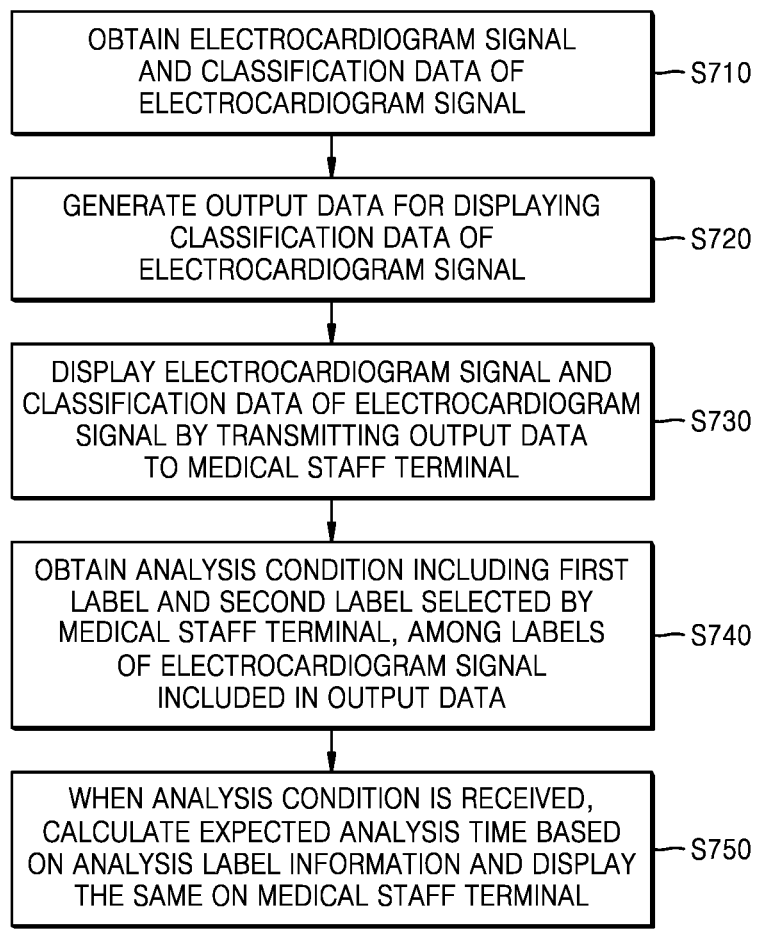
FIG. 11 is a flowchart of a method of calculating expected analysis time based on an analysis condition input as a label according to one or more embodiments.

The electrocardiogram data processing system 1 may refer to a system configured to process an electrocardiogram signal and classification data of the electrocardiogram signal and may generate a label in relation to heart rates and/or the electrocardiogram signal by analyzing the electrocardiogram signal. Here, the label may be generated as shown in FIG. 11.

The electrocardiogram data processing system 1 may generate a label classified by a predetermined category value for an electrocardiogram signal, which is a signal about the heart. Such data including a label may be referred to as classification data.

The electrocardiogram data processing server 10 may obtain the electrocardiogram signal and label information of the electrocardiogram signal and may be implemented to perform an additional analysis process in this regard. The electrocardiogram data processing server 10 may calculate an expected analysis time of the electrocardiogram signal based on a label of the electrocardiogram signal and an analysis condition of a medical staff. An algorithm for calculating the expected analysis time may be generated by a certain method, such as machine-learning, intensive learning, supervised learning, unsupervised learning, etc. The algorithm for calculating the expected analysis time may be updated by input data. In this manner, the time required to analyze electrocardiogram data may be identified by calculating in advance an expected analysis time before analyzing the electrocardiogram data. A medical staff may identify time and costs required to analyze the electrocardiogram data. An analyst may also analyze the electrocardiogram data knowing the expected analysis time beforehand and plan in advance a business process regarding one or more pieces of electrocardiogram data. The electrocardiogram data processing server 10 may provide data about the calculated expected analysis time to a medical staff terminal 21, receive a modified analysis condition from the medical staff terminal 21, recalculate an expected analysis time based on the modified analysis time, and generate data regarding the expected analysis time. When a request to confirm the analysis condition is received from the medical staff terminal 21, the electrocardiogram data processing server 10 may transmit the analysis request according to the analysis condition to an analyst terminal 22. And, the analyst may conduct an analysis process with respect to a section of the electrocardiogram signal according to the analysis condition. In this manner, the medical staff may control the expected analysis time. When the expected analysis time is too long, the medical staff may reduce the expected analysis time by modifying the analysis condition. When the expected analysis time is less than a preset value, the analysis condition may be modified so that more signal sections may be analyzed.

In another embodiment, when a desired expected analysis time is received by the medical staff or analyst, an analysis condition corresponding to the desired expected analysis time may be determined, and data regarding the analysis condition may be transmitted to the medical staff terminal or the analyst terminal. The data (or parameters) regarding the analysis condition may include signal segments corresponding to the analysis condition and the expected analysis time required to analyze the signal segments. The electrocardiogram data processing server 10 may return an analysis condition for the desired expected analysis time by using a machine-trained model, function, etc., based on the analysis condition and analysis time required for analysis of the electrocardiogram signal.

The electrocardiogram data processing server 10 may extract interval sections from the electrocardiogram signal and may extract label corresponding to each section of the electrocardiogram signal by using morphological characteristics (peak points, a slope of a signal, a signal width, etc.) in the interval sections. The electrocardiogram data processing server 10 may perform a classification process to add a label corresponding to each section of the electrocardiogram signal. The classification process may be performed according to a certain algorithm, and the algorithm may be generated through learning, for example, various types of machine-learning algorithms, intensive learning algorithms, and neural networks. The algorithm may be changed to an algorithm having a higher prediction probability when the amount of input data increases.

The electrocardiogram data processing server 10 may display the electrocardiogram signal and label information of the electrocardiogram signal on an output portion of the medical staff terminal 21, the analyst terminal 22, and another user terminal connected to the electrocardiogram data processing server 10. FIG. 1 illustrates one medical staff terminal and one analyst terminal; however, the present disclosure is not limited thereto, and a plurality of medical staff terminals and/or a plurality of analyst terminals may be connected to and communicate with each other. The electrocardiogram data processing server 10 may be implemented in one computing device or implemented in a plurality of distributed computing devices.

The electrocardiogram data processing server 10 may generate an electrocardiogram analysis data according to an analysis condition from the plurality of medical terminals. Here, the analysis condition is for selecting signal segments to be analyzed from among the electrocardiogram signals, and one or more values or morphological characteristics such as a label, data value, signal interval, signal interval, pulse rate, respiration rate, and signal to be analyzed may contain itself. The electrocardiogram analysis data according to the analysis condition may be generated in one analyst terminal 22 selected from the plurality of analyst terminals.

Here, although a method of storing electrocardiogram data stored in the electrocardiogram data processing server 10 is omitted for convenience in explanation, it is obvious that a measurer or a medical staff may store the electrocardiogram data or the electrocardiogram data may be automatically stored in an electrocardiogram measuring device.

According to embodiments, the electrocardiogram data processing server 10 may calculate an expected analysis time according to the electrocardiogram signal and classification data of the electrocardiogram signal. The electrocardiogram data processing server 10 may calculate a first analysis time for each section of the electrocardiogram signal. The electrocardiogram data processing server 10 may calculate an expected analysis time for the electrocardiogram signal based on the calculated first analysis times. The electrocardiogram data processing server 10 may calculate the expected analysis time by excluding noise sections included in the electrocardiogram signal, calculating a second analysis time of the noise sections based on signal lengths of the noise sections, and further aggregating the second analysis times. The electrocardiogram data processing server 10 may determine a section of interest. By selecting data of interest corresponding to the section of interest, an expected analysis time of the data of interest may be re-calculated. The section of interest may be determined within the electrocardiogram signal by medical questionnaire items, classification data of the electrocardiogram signal, analysis condition input by medical team, analyst, etc. Here, the section of interest may include a section of the electrocardiogram signal measured at a specified period and time. The section of interest may refer to a section designated by various conditions. For example, the section of interest may be determined to be at least one day (24 hours) set in a measurement period during which the electrocardiogram signal is measured. The processor 120 may determine whether the expected analysis time is less than a preset target time. When the expected analysis time is less than the target time, the analysis of the electrocardiogram signal may be transmitted to the analyst terminal and performed. The expected analysis time may be the time required for analyzing the electrocardiogram signal and may be calculated by various algorithms. Here, the expected analysis time according to the analysis condition refers to an expected value or a predicted value for time required to analyze the electrocardiogram signal corresponding to the preset analysis condition. The target time may be a desired expected analysis time. The target time may be a time for analyzing the electrocardiogram signal, and may be determined by an internal algorithm of a server, an algorithm of an external device, or a value input through other devices (e.g., a medical staff terminal, an analyst terminal, etc.) The electrocardiogram data processing server 10 may calculate the expected analysis time considering the analysis condition among classification data of the electrocardiogram signal. The analysis condition may be modified by the medical staff terminal. The electrocardiogram data processing server 10 may transmit, to the medical staff terminal, result data regarding whether the expected analysis time is less than a preset target time. The classification data of the electrocardiogram signal may be generated by classifying the sections of the electrocardiogram signal into the labels defined in FIG. 14; however, the disclosure is not limited thereto.

The medical staff terminal 21 may access the electrocardiogram data processing server 10 and receive an analysis condition regarding a registered user's electrocardiogram signal. The medical staff terminal 21 may receive an expected analysis time according to the analysis condition. The electrocardiogram analysis data may refer to data obtained by analyzing signal sections corresponding to analysis conditions. The medical staff terminal 21 may check the expected analysis time and enter a user input modifying the analysis condition. The medical staff terminal 21 may receive electrocardiogram analysis data analyzed according to the user input. The medical staff terminal 21 may receive a report about data according to the analysis condition.

The analyst terminal 22 may access the electrocardiogram data processing server 10 and may receive the classification data of the electrocardiogram signal from user. The electrocardiogram data processing server 10 may provide user interface data for analyst to check the analysis data, and may periodically provide the analyst analysis data to the medical staff terminal 21, which has a certain authority.

The analysis data may include an analysis condition, time consumed in analysis of the electrocardiogram signal, information about a responsible and analysis module, information about labels generated based on the analysis, unusual signal section, etc.

The electrocardiogram data processing system 1 may be connected to the analyst terminal 22 and the medical staff terminal 21 through a network to receive and transmit data between them.

Figure 2:
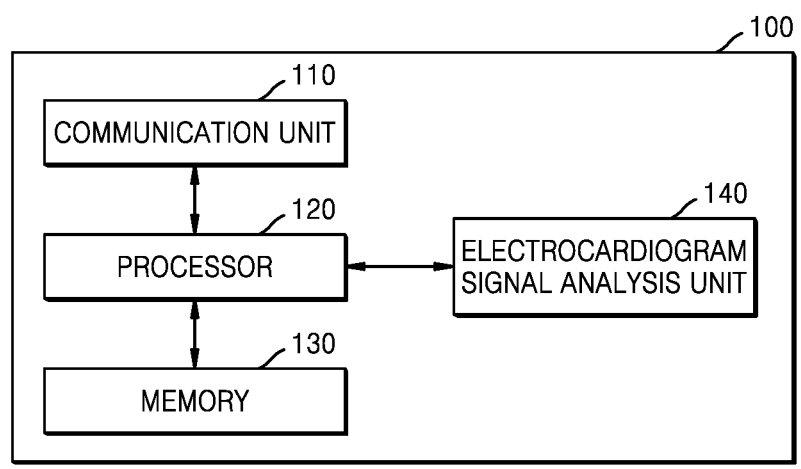
FIG. 2 is a block diagram of an electrocardiogram data processing server according to one or more embodiments.

FIG. 2 is a block diagram of an electrocardiogram data processing server 100 according to embodiments.

The electrocardiogram data processing server 100 may include a communicator 110, a processor 120, a memory 130, and an electrocardiogram signal analyst 140. However, not all of the components illustrated in FIG. 2 are essential components of the electrocardiogram data processing server 100. The electrocardiogram data processing server 100 may be implemented by more or less components than the components illustrated in FIG. 2. The electrocardiogram data processing server 100 may be a user terminal, a server, a system, or a separate device. Moreover, the electrocardiogram data processing server 100 may be implemented by a cloud system. The electrocardiogram data processing server 10 of FIG. 1 may be replaced with the electrocardiogram data processing server 100 of FIG. 2. The electrocardiogram data processing server 10 of FIG. 1 may have the same structure as the electrocardiogram data processing server 100. When the electrocardiogram data processing server 100 is implemented by a cloud system, the analyst and the medical staff may be located in the same position or each in different positions.

In general, the processor 120 may control all operations of the electrocardiogram data processing server 100. For example, the processor 120 may execute a program stored in the electrocardiogram data processing server 100 to control all components included in the electrocardiogram data processing server 100.

According to an embodiment, the processor 120 may calculate the expected analysis time according to the electrocardiogram signal and the classification data of the electrocardiogram signal. For example, the processor 120 may calculate the expected analysis time by using the analysis time required to verify the signal of the first label among the classification data. The processor 120 may calculate a first analysis time for each section of the electrocardiogram signal. The processor 120 may calculate an expected analysis time for the electrocardiogram signal based on the calculated first analysis times. The processor 120 may calculate the expected analysis time by excluding noise sections included in the electrocardiogram signal, calculating a second analysis time of the noise sections based on signal lengths of the noise sections, and further aggregating the second analysis times. The processor 120 may determine a section of interest, which is a part of the electrocardiogram signal, select data of interest corresponding to the section of interest, and calculate an expected analysis time of the data of interest. The section of interest may be determined to be at least one first date set in a measurement period during which the electrocardiogram signal is measured. Here, the expected analysis time is calculated based on the section of interest. The expected analysis time may be the time required for analyzing the electrocardiogram signal and may be calculated by various algorithms. The target time may be the desired expected analysis time. The target time may be a time for analyzing the electrocardiogram signal, and may be determined by an internal algorithm of a server, an algorithm of an external device, or a value input through other devices. The processor 120 may calculate the expected analysis time considering the analysis condition among the classification data of the electrocardiogram signal. The processor 120 may transmit, to the medical staff terminal result data about whether the expected analysis time is within a preset target time.

According to an embodiment, the processor 120 may receive, from the medical staff terminal, the analysis condition of the electrocardiogram signal. The processor 120 transmits the result data of comparing the expected analysis time with the target time to the medical staff terminal, so that the analysis condition and the section of interest are modified so that the analysis is completed in less than the target time. The processor 120 may extract sections corresponding to the analysis condition and calculate the expected analysis time of sections corresponding to the analysis condition considering the occurrence patterns and analysis time of the sections.

Figure 14:
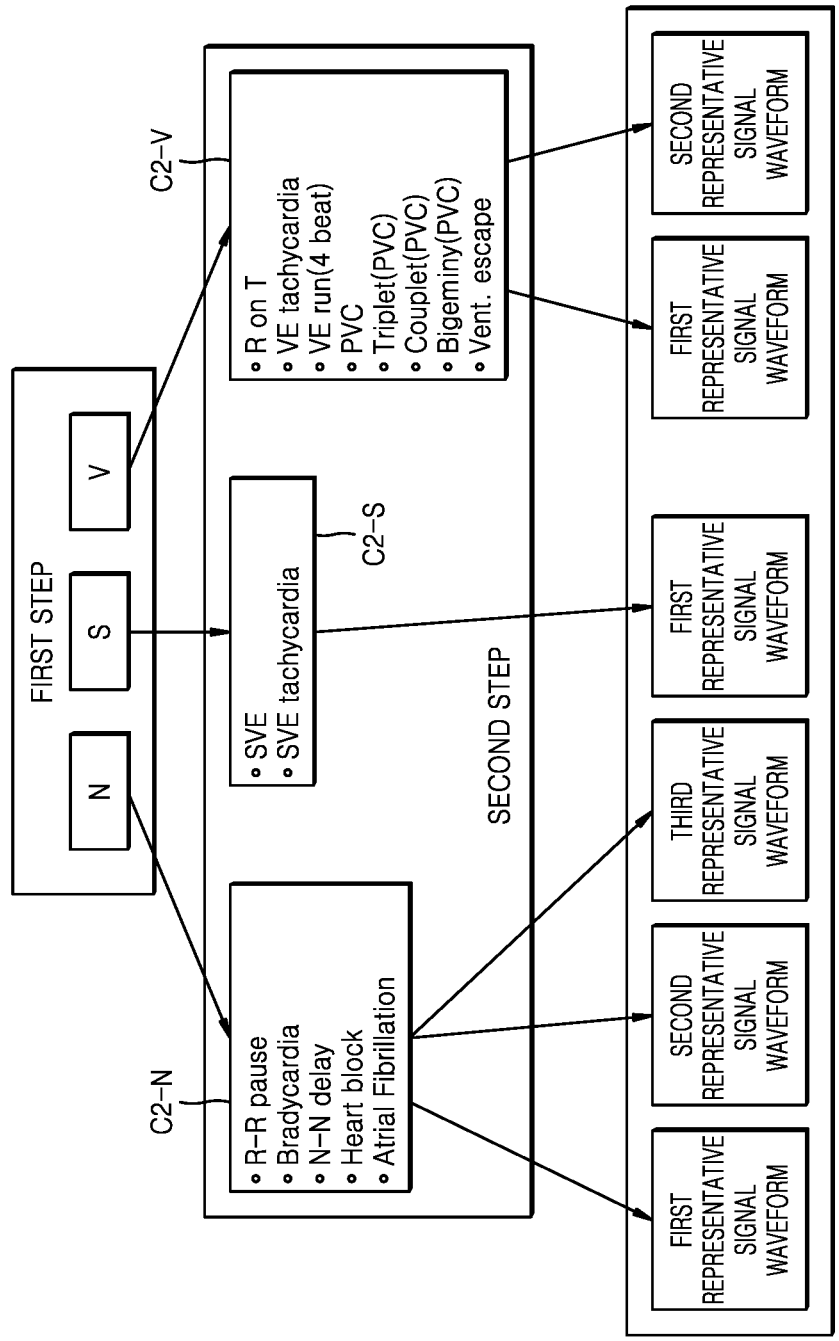
FIG. 14 is a diagram illustrating an example of a label included in classification data of an electrocardiogram signal according to one or more embodiments.

The processor 120 may provide, to the user terminal, the classification data of the electrocardiogram signal and input the analysis condition based on a section signal for the provided classification data. The classification data of the electrocardiogram signal may include an electrocardiogram signal, heart rates of the electrocardiogram signal, a category value of each section of the electrocardiogram signal, a label for the category value, etc. Category values and labels for the category values may be as shown in FIG. 14. The analysis condition may be set as one or more labels, or a particular time section. The analysis condition may come from a disease, illness, etc. and convert into one or more labels.

The processor 120 may transmit an analysis request signal for the electrocardiogram signal to the analyst terminal or the analysis module so that an analysis comment on the electrocardiogram signal is received from the analyst terminal or the analysis module. The analysis request signal may include sections corresponding to the analysis condition, in the electrocardiogram signal. The analysis request signal may be generated by an approval signal regarding the analysis request from the medical staff terminal and transmitted. The processor 120 may analyze sections for an analysis condition of a pre-stored default value. The default value may be a value predetermined in advance. An approval signal for an analysis request may be generated without an additional input by the medical staff.

The processor 120 may display a first window displaying the analysis data of the electrocardiogram signal and a second window displaying the expected analysis time. The electrocardiogram signal or the analysis data of the electrocardiogram signal may be included in the first window of day (24 hours) unit. The expected analysis time may be classified and included in the second window per day. The processor 120 may calculate the expected analysis time by using the analysis data of the electrocardiogram signals performed previously and the classification data of the electrocardiogram signal. The processor 120 may receive data regarding the analysis times of the electrocardiogram signals previously performed by a plurality of analysts or a plurality of analysis modules registered with the server. The processor 120 may convert the received data into a predetermined data structure and store it in the memory. Here, the analysis data includes data generated when the analysis of electrocardiogram signals measured in the past is completed, and refers to data uploaded to the electrocardiogram data processing server 100. The analysis data may further include object information of the electrocardiogram signal, analyst information, analysis time required for analysis, a measurement device (model, software version, etc.), possessed diseases, and the like. The electrocardiogram data processing server 100 may generate an algorithm, an equation, a table, a function, etc. by using the measured electrocardiogram signals and the analysis data for the electrocardiogram signals. Algorithms, equations, tables, functions, etc. may vary depending on the analyst, the measuring device, the disease, and the like. The processor 120 may process one or more windows displaying analysis processed data corresponding the data to be displayed on the user terminal. In response to an input value selecting an analyst or an analysis module, the processor 120 may control the second window to display the expected analysis time for the case where the analysis of the electrocardiogram signal is performed by the selected analyst or analysis module.

The processor 120 may calculate at least one of duration, symptom value, and label value of each signal section, and set, among the calculated information, first information as display set information and the rest of the information as hidden set information. The processor 120 may generate output data to classify the electrocardiogram signals as the first information, which is display information set, and output the same. The first information may be classified based on a measurement day.

The processor 120 may display a plurality of duration values, unusual symptoms, reference waveforms, etc. set with respect to the electrocardiogram signals on a list screen and when an input to select a first value among the plurality of duration values, unusual symptoms, and reference waveforms is detected, the processor 120 may set the first value as the display set information. The processor 120 may process the signal sections corresponding to the first value to be displayed all at once by the external terminal. When a report signal for the analysis request signal is received, the processor 120 may transmit, to the medical staff terminal, output data according to the report signal, and when a confirm signal for the output data is received from the medical staff terminal, a state of the analysis request signal may be changed to a complete state.

The processor 120 may be a component configured to control the electrocardiogram data processing server 100 in general. More specifically, the processor 120 may control all operations of the electrocardiogram data processing server 100 by using various programs stored in a storage medium of the electrocardiogram data processing server 100. For example, the processor 120 may include a central processing unit (CPU), random-access memory (RAM), read-only memory (ROM), a system bus, etc. The ROM may be a component in which a command set for system booting is stored, the CPU may copy an operating system stored in the electrocardiogram data processing server 100 to the RAM according to a command stored in the ROM and execute the operating system to boot a system. When the booting of the system is completed, the CPU may copy various stored applications to the RAM and execute them to perform various operations. Although the electrocardiogram data processing server 100 is described as including one CPU, the service providing server 100 may be implemented by a plurality of CPUs (or a digital signal processor (DSP), a System-on-Chip (SoC), etc.)

According to an embodiment, the processor 120 may be implemented by a DSP configured to process digital signals, a microprocessor, and a time controller (TCON). However, the disclosure is not limited thereto, and the processor 120 may include one or more of a CPU, a micro controller unit (MCU), an application processor (AP), a communication processor (CP), and an ARM processor and may be defined by such corresponding term. Moreover, the processor 120 may be implemented by an SoC or large scale integration (LSI) embedded with a processing algorithm, and may be implemented in the form of a field programmable gate array (FPGA).

According to an embodiment, the memory 130 may store a program for processing and control by the processor 120 and/or the electrocardiogram signal analyst 140 and store data input to the electrocardiogram data processing server 100 or data output from the electrocardiogram data processing server 100. According to an embodiment, the memory 130 may store the electrocardiogram signal and the classification data of the electrocardiogram signal. The memory 130 may store data regarding the input analysis condition. The memory 130 may store data required for generating output data regarding the electrocardiogram signal.

According to an embodiment, the memory 130 may include a storage medium of at least one type, including memory of flash memory type, hard disk type, multimedia card micro type, memory of card type (e.g., SD or XD memory, etc.), RAM, static RAM, ROM, electrically erasable programmable ROM, PROM, magnetic memory, a magnetic disk, and an optical disk. Furthermore, according to an embodiment, the programs stored in the memory 130 may be classified into a plurality of modules according to their functions.

According to an embodiment, the communicator 110 may perform communication with an external device outside the processor 120. For example, the communicator 110 may perform communication with an external device, such as a user terminal and other servers according to the control by the processor 120. Moreover, the communicator 110 may obtain user information or a user input through communication with an external interface. The electrocardiogram data processing server 100 may be a cloud system, and a network by the communicator 110 may be an intranet/internet. The communications security and electrocardiogram signal security may be implemented by various methods.

Figure 3:
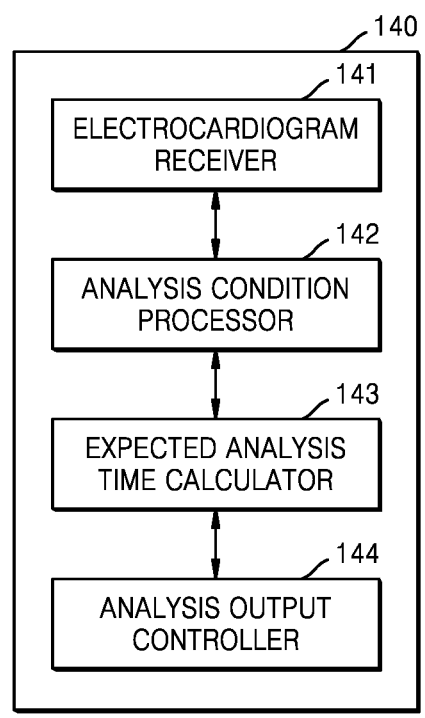
FIG. 3 is a block diagram of an electrocardiogram signal analysis unit according to one or more embodiments.

FIG. 3 is a block diagram of the electrocardiogram signal analyst 140 according to embodiments.

The electrocardiogram signal analyst 140 may include an electrocardiogram receiver 141, an analysis condition processor 142, an expected analysis time calculator 143, and an analysis output controller 144.

The electrocardiogram receiver 141 may receive data of the electrocardiogram signal. The data of the electrocardiogram signal may include the electrocardiogram signal and the classification data of the electrocardiogram signal. The data of the electrocardiogram signal may be data regarding the electrocardiogram signal measured for a certain period, for example, for one week, 14 days, etc. The classification data of the electrocardiogram signal may include a category value time-sequentially displaying signal waveforms of the electrocardiogram signal and corresponding to each signal waveform. The category value may be a value converted into a label. The category value may include R-R Pause, Bradycardia, N-N delay, Heart Block, Atrial Fibrillation (AF), SVE, SVE tachycardia, R on T, VE tachycardia, VE run, PVC, Triplet (PVC), Couplet (PVC), Bigeminy (PVC), Ventricular Escape, etc.; however, the disclosure is not limited thereto, and the category value may have various values. Such category values may be converted into labels corresponding thereto, and be included in the analysis data of the electrocardiogram signal.

In another embodiment, the electrocardiogram receiver 141 may analyze the signal waveforms of the electrocardiogram signal by using the data regarding the received electrocardiogram signal and generate the classification data of the electrocardiogram signal. The electrocardiogram receiver 141 may divide the electrocardiogram signal into segments, and classify the electrocardiogram signal by setting each segment as one of category values to generate the classification data of the electrocardiogram signal.

The analysis condition processor 142 may transmit electrocardiogram output data displaying the electrocardiogram signal and the classification data of the electrocardiogram signal to an external terminal. The electrocardiogram output data may be displayed on the external terminal by the analysis condition processor 142. The analysis condition may be input based on an input interface of the analysis condition included in the electrocardiogram output data by the analysis condition processor 142. The analysis condition processor 142 may generate the electrocardiogram data displaying past medical history, current medical questionnaire items and responses thereto, etc. regarding an object. The medical questionnaire items may be data including answers of the object to inquiries prepared by the medical staff. The medical questionnaire items or the response thereto may include information about pains related to the heart. The analysis condition processor 142 may determine one or more labels related to the past medical history, current medical questionnaire items, etc. of the object by using a table showing a relation between medical history and labels and search sections of the electrocardiogram signal for labels related to the past medical history, medical questionnaire items, etc. to generate output data of the sections of the electrocardiogram signal. Table showing a relation between the medical history and the label may be stored inside the electrocardiogram data processing server 100 or in an external device and may be received through a network. The table showing a relation between the medical history and the label may be modified by an input electrocardiogram signal, medical history information of an object, etc. The table showing a relation between the medical history (kinds of disease/symptom, time of occurrence, etc.) and the label may be modified by an expert. Data about labels related to other living characteristics information and bio-information (e.g., age, gender, dwelling, occupation, race, smoking status, alcohol use, etc.) of an object may be generated and managed. Moreover, the medical staff may add an additional label from an object of electrocardiogram measurement through a medical questionnaire (e.g., the time at which an object feels discomfort and symptoms of the discomfort). The analysis condition processor 142 may determine a label with respect to the object based on the aforementioned information and generate data regarding sections classified by the label.

The electrocardiogram output data may list the electrocardiogram signal per label and display the same. For example, the electrocardiogram output data may provide sections of the electrocardiogram signal classified into a first label, a second label, a third label, etc. The sections classified as the first label, the sections classified as the second label, and the sections classified as the third label may be displayed all at once or distinguishable from each other.

The electrocardiogram output data may include data listed according to the priorities. The analysis condition processor 142 may determine a priority among labels based on the information regarding the measured object, and the section data of each label may be displayed according to the priority. For example, the analysis condition processor 142 may set a priority in relation to sections according to past medical history, current medical questionnaire result, use of alcohol, smoking status, gender, age, etc. The priority may be set for each label, but is not limited thereto, and may be set. The analysis condition processing unit 142 may generate section data in which a section having a high priority is arranged in a priority order. The priority may be used in the process of estimating the analysis time.

The medical staff terminal 21 may access the electrocardiogram data processing server 100, receive the electrocardiogram output data including the electrocardiogram signal and the classification data of the electrocardiogram signal, and input the analysis condition corresponding to the classification data of the electrocardiogram signal. At least one of a label set, time, disease, illness, etc. may be set as the analysis condition. The first label and the second label may be set as the analysis condition. The analysis condition processor 142 may separately search for and provide sections including a preset analysis condition. The analysis condition processing unit may generate location information of sections of the first and second labels, and generate signal sections of the first and second labels as data based on the locations. According to the preset analysis condition set by the label set and time, the analysis condition processor 142 may generate data regarding signal sections corresponding to the analysis condition. When the analysis condition includes kinds of disease or illness, the analysis condition processor 142 may determine labels related to diseases or illnesses and convert the labels into the analysis condition.

The analysis condition processor 142 may classify the electrocardiogram signal on a certain time basis, for example, by the unit of day or week, according to the analysis condition, and generate data corresponding to the daily analysis condition. The analysis condition processor 142 may transmit the data corresponding to the daily analysis condition to an external terminal. On the external terminal, the data corresponding to the daily analysis condition may be displayed. As human biorhythm has a circadian period, the measured electrocardiogram signal may be displayed on a daily basis, i.e., circadian. Furthermore, the medical questionnaire data regarding the object may be generated on a daily basis. The object may also remember symptoms, pain, etc. on a daily basis, i.e., fora period of 24 hours.

The analysis condition processor 142 may extract period information of the analysis condition from the electrocardiogram signal. The expected analysis time calculator 143 may calculate the expected analysis time considering the period information of sections corresponding to the analysis condition and analysis time of a section corresponding to each analysis condition. The expected analysis time calculator 143 may calculate the expected analysis time by multiplying the period of occurrence of section by analysis time of the section. The expected analysis time calculator 143 may determine an occurrence pattern of the section corresponding to the analysis condition and calculate the expected analysis time according to the occurrence pattern. The expected analysis time may be set to include a range between a minimum time and a maximum time. The expected analysis time calculator 143 may calculate the analysis time of the section corresponding to the analysis condition by using machine-learned data, algorithms, etc. Furthermore, the expected analysis time calculator 143 may calculate the analysis time of the section corresponding to the analysis condition based on the performance history of the analyst. The expected analysis time calculator 143 may determine the analysis time of the section corresponding to the analysis condition based on the performance histories of other analysts.

The expected analysis time calculator 143 may calculate noise duration, among parameters used for analysis time estimation to determine a ratio of the noise duration, and calculate the expected analysis time. The noise may occur during the measurement of the electrocardiogram signal and included in the electrocardiogram signal, and may be caused due to movements of an object, a voltage, etc., from other muscles generated by such movement. The noise may be generated by a conflict of static and electrical signals inside an electrocardiogram measuring device. The noise may be caused by change in connection relation between the electrocardiogram measuring device and the target. For example, the noise may include change in a voltage value caused by factors other than cardiac movements. As the noise included in the electrocardiogram signal may affect the analysis time of the electrocardiogram signal, a search for information about the noise may be required when calculating the expected analysis time. The expected analysis time calculator 143 may transmit data regarding the calculated expected analysis time to an external terminal.

The expected analysis time calculator 143 may analyze an occurrence pattern of the noise and calculate the expected analysis time based thereon. The occurrence pattern of the noise may be in accordance with a rule among the times of noise occurrence.

The expected analysis time calculator 143 may extract noise durations from the analysis data of the electrocardiogram signal and determine whether a ratio of the extracted noise durations is greater or less than a preset reference ratio value. The expected analysis time calculator 143 may calculate noise duration and a ratio of the noise duration with respect to the entire or a part of the electrocardiogram signal. A measurement target signal may include signal sections classified by the analysis condition. The reference ratio value may be set by the connected medical staff.

The expected analysis time calculator 143 may transmit the data regarding the calculated noise duration and the ratio value of the noise duration to an external terminal. The data regarding the noise may be displayed on the external terminal. A modification input for the noise duration data may be made to the external terminal and the expected analysis time calculator 143 may receive the modification input and perform a process corresponding to the modification input.

When the modification input is an input to modify the analysis condition or the analysis section, the expected analysis time calculator 143 may obtain again, in response to the modification input, the analysis target signal to be analyzed in correspondence with the analysis condition or the analysis section and recalculate the noise duration and the ratio of the noise duration with respect to the analysis target signal. The noise duration may be excluded to determine the expected analysis time.

When the modification input is an input to modify the target time, the expected analysis time calculator 143 may generate output data with a modified target time in response to the modification input. The analysis request signal for the electrocardiogram signal may be generated based on the modified target time.

The medical staff terminal 21 may input the modification input for the analysis condition by conducting a medical questionnaire with the object. By learning symptom (discomfort) sensing information such as symptom (discomfort) duration, sensing time section, etc. by the medical questionnaire, the analysis condition may be modified so that such time information is analyzed. The symptom (discomfort) sensing information may be obtained by a medical questionnaire performed on a patient by the medical staff, or may be generated by an input by the patient during the measurement of the electrocardiogram signal. The symptom sensing information may be generated by measured bio-information. The measured bio-information may include a respiration/pulse value, movement value, noise value, blood pressure value, blood glucose value, food intake, exercise level, stress index, time/quality of sleep, etc. When the symptom (discomfort) information is generated by an input or bio-information during the electrocardiogram signal is measured, the symptom (discomfort) information may be included in the electrocardiogram signal. Moreover, when an urgent analysis is required, an analysis time necessary for analysis of the electrocardiogram signal having a certain designated period may be calculated.

The analysis condition may be set by combining various conditions. For example, the analysis condition may be set as ventricular fibrillation or atrial block under a certain heart rate, which may lead to a cardiac arrest, or ventricular tachycardia with a high heart rate, etc. The analysis condition may be converted into corresponding sections included in the electrocardiogram signal. The expected analysis time calculator 143 may calculate the expected analysis time of the electrocardiogram signal based on the noise pattern of the electrocardiogram signal. The expected analysis time calculator 143 may exclude noise sections for the electrocardiogram signal, calculate the analysis time of the noise sections based on signal lengths of the noise sections, and calculate the expected analysis time based on the analysis time of the noise sections. The expected analysis time calculator 143 may select data of interest of the electrocardiogram signal corresponding to the section of interest and calculate the expected analysis time of the data of interest. The section of interest may be determined by a certain condition from the measurement period. The expected analysis time calculator 143 may calculate the expected analysis time based on the occurrence pattern of the section corresponding to the analysis condition for the electrocardiogram signal. The expected analysis time calculator 143 may calculate the expected analysis time considering the noise pattern and occurrence pattern in the section corresponding to the analysis condition. The expected analysis time calculator 143 may calculate the analysis time for the noise by using the machine-learned data. Furthermore, the expected analysis time calculator 143 may calculate the analysis time of the noise based on the performance history of the analyst. The expected analysis time calculator 143 may calculate the analysis time of the noise based on the performance histories of other analysts.

The analysis output controller 144 may display a first window displaying the analysis data of the electrocardiogram signal and a second window displaying the expected analysis time. The electrocardiogram signal or the analysis data of the electrocardiogram signal may be included in the first window of day or 24 hours unit. The expected analysis time may be classified and included in the second window per day. The analysis output controller 144 may calculate the expected analysis time by using the analysis data of the electrocardiogram signals performed previously and the classification data of the electrocardiogram signal. The analysis output controller 144 may generate data regarding the analysis times of the electrocardiogram signals previously performed by a plurality of analysts or a plurality of analysis modules registered with the server. The analysis output controller 144 may process a window displaying analysis processed data corresponding the data to be displayed on the user terminal. When an input to select an analyst is obtained by a user, the analysis output controller 144 may control the second window to display the expected analysis time for the case where the analysis of the electrocardiogram signal is performed by the selected analyst.

The analysis output controller 144 may calculate at least one of duration, symptom value, and label value of each signal section, and set, among the calculated information, first information as display set information and the rest of the information as hidden set information. The analysis output controller 144 may generate output data to classify the electrocardiogram signals as the first information, which is display set information, and output the same. The first information may be classified based on a measurement day.

The analysis output controller 144 may display a plurality of duration values, unusual symptoms, reference waveforms, etc. set with respect to the electrocardiogram signals on a list screen and when an input to select a first value among the plurality of duration values, unusual symptoms, and reference waveforms is detected, the processor 120 may set the first value as the display set information. The analysis output controller 144 may process the signal sections corresponding to the first value to be displayed all at once in the user terminal. When a report signal for the analysis request signal is received, the analysis output controller 144 may transmit, to the medical staff terminal, output data according to the report signal, and when a confirm signal for the output data is received from the medical staff terminal, a state of the analysis request signal may be changed to a complete state.

Figure 4:
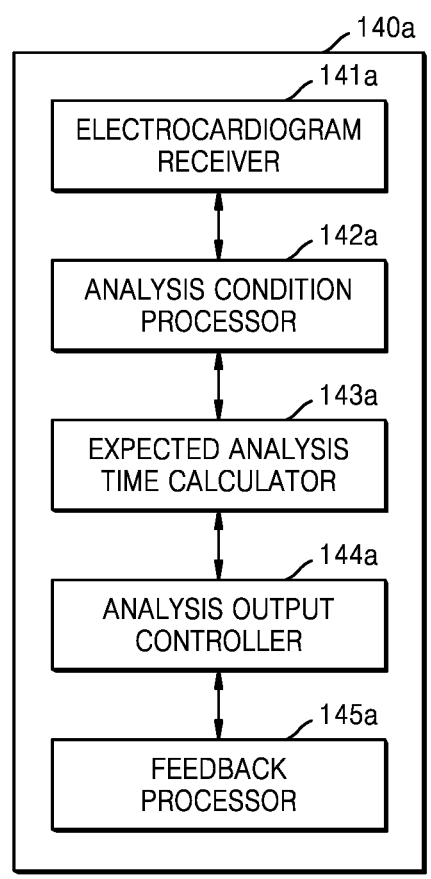
FIG. 4 is a block diagram of an electrocardiogram signal analyst configured to generate an electrocardiogram analysis request by using a feedback from an analyst terminal according to one or more embodiments.

FIG. 4 is a block diagram of an electrocardiogram signal analyst 140a configured to generate an electrocardiogram analysis request by using a feedback from an analyst terminal, according to other embodiments.

The electrocardiogram signal analyst 140a may be an alternative of the electrocardiogram signal analyst 140.

The electrocardiogram signal analyst 140a may include an electrocardiogram receiver 141a, an analysis condition processor 142a, an expected analysis time calculator 143a, an analysis output controller 144a, and a feedback processor 145a.

The electrocardiogram receiver 141a may receive data of the electrocardiogram signal. The data of the electrocardiogram signal may include the electrocardiogram signal and the classification data of the electrocardiogram signal. The data of the electrocardiogram signal may be data regarding the electrocardiogram signal measured for a certain period, for example, for one week, 14 days, etc. The classification data of the electrocardiogram signal may include a category value time-sequentially displaying signal waveforms of the electrocardiogram signal and corresponding to each signal waveform. The category value may be a value converted into a label. The category value may include R-R Pause, Bradycardia, N-N delay, Heart Block, Atrial Fibrillation (AF), SVE, SVE tachycardia, R on T, VE tachycardia, VE run, PVC, Triplet (PVC), Couplet (PVC), Bigeminy (PVC), Ventricular Escape, etc.; however, the disclosure is not limited thereto, and the category value may have various values. Such category values may be converted into labels corresponding thereto, and be included in the classification data of the electrocardiogram signal.

In another embodiment, the electrocardiogram receiver 141a may analyze signal waveforms of the electrocardiogram signal and generate the classification data of the electrocardiogram signal. The electrocardiogram receiver 141a may divide the electrocardiogram signal into signal segments by a signal waveform, and classify the electrocardiogram signal by setting each segment as one of category values to generate the classification data of the electrocardiogram signal.

The analysis condition processor 142a may transmit the electrocardiogram signal and the classification data of the electrocardiogram signal to an external terminal, and the analysis condition for the electrocardiogram signal is input from the external terminal so that the data about the analysis condition may be received. The analysis condition may include information about label, time, disease, symptom, illness, etc.

When the data regarding the analysis condition is received, the analysis condition processor 142a may separate search and provide the sections including the preset analysis condition. The analysis condition processor 142a may generate data regarding sections including the first label and second label and positions thereof. According to the preset analysis condition set by the label set and time, the analysis condition processor 142a may generate data regarding signal sections corresponding to the analysis condition. When the analysis condition includes kinds of disease or illness, the analysis condition processor 142a may determine labels related to diseases or illnesses and convert the labels into the analysis condition. The analysis condition processor 142a may use the screen displayed on the external terminal so that the analysis condition is input from the external terminal. The analysis condition processor 142a may determine a label, analysis section, etc. with respect to the object according to the analysis condition obtained from the analysis output controller 144a and generate data about the sections classified by a label and analysis section.

The analysis condition processor 142a may classify the electrocardiogram signal on a certain time basis, for example, by the unit of day or week, according to the analysis condition, and generate data corresponding to the daily analysis condition. The analysis condition processor 142a may transmit the data corresponding to the daily analysis condition to an external terminal. On the external terminal, the data corresponding to the daily analysis condition may be displayed.

The analysis condition processor 142a may extract period information of the analysis condition from the electrocardiogram signal. The expected analysis time calculator 143a may calculate the expected analysis time considering the period information of sections corresponding to the analysis condition and analysis time of a section corresponding to each analysis condition. The expected analysis time calculator 143a may calculate the expected analysis time by multiplying the period of occurrence of section by analysis time of the section. The expected analysis time calculator 143a may determine an occurrence pattern of the section corresponding to the analysis condition and calculate the expected analysis time according to the occurrence pattern. The expected analysis time may be set to include sections of a minimum value and a maximum value.

The expected analysis time calculator 143a may use noise duration by priority, among parameters used for analysis time estimation. The noise duration may be excluded from the analysis or used in association with other bio-signals (e.g., movement).

The expected analysis time calculator 143a may analyze an occurrence pattern of the noise and calculate the expected analysis time based thereon. The occurrence pattern of the noise may be in accordance with a rule among the times of noise occurrence. The occurrence pattern of the noise may vary according to the cause of noise. When the noise is generated due to deteriorated attachment of an electrocardiogram measuring electrode on the skin, such noise may not be subject to the electrocardiogram signal analysis; however, depending on whether the noise is generated due to a movement of an object (e.g., a signal generated from muscles during sleep or exercise), the arrhythmia may be diagnosed by using the heart rate obtained from the electrocardiogram signal.

The expected analysis time calculator 143a may exclude noise durations from the analysis data of the electrocardiogram signal and determine whether a ratio of the noise durations is greater or less than a preset reference ratio value. The expected analysis time calculator 143 may calculate noise duration and a ratio of the noise duration with respect to the entire or a part of the electrocardiogram signal. A measurement target signal may include signal sections classified by the analysis condition. The reference ratio value may be set by the connected medical staff.

The expected analysis time calculator 143a may transmit the data regarding the calculated noise duration and the ratio value of the noise duration to an external terminal. The data regarding the noise may be displayed on the external terminal. A modification input for the noise duration data may be given in the external terminal and the expected analysis time calculator 143a may receive the modification input and perform a process corresponding to the modification input.

When the modification input is given to modify the analysis section or the analysis condition, the expected analysis time calculator 143a may obtain again, in response to the modification input, the analysis target signal to be analyzed in correspondence with the analysis section or the analysis condition and recalculate the noise duration and the ratio of the noise duration with respect to the analysis target signal. During this process, various analysis conditions may be set according to a cause of noise.

When the modification input is an input to modify the target time, the expected analysis time calculator 143a may generate output data with a modified target time in response to the modification input. The analysis request signal for the electrocardiogram signal may be generated based on the modified target time.

The medical staff terminal 21 may input the modification input for the analysis condition by conducting a medical questionnaire with the object. By learning symptom (discomfort) sensing information such as symptom (discomfort) duration, sensing time section, etc. by the medical questionnaire, the analysis condition may be modified so that such time information is analyzed. The symptom (discomfort) sensing information may be obtained from a patient by the medical staff, and may be generated by an input by the patient during the measurement of the electrocardiogram signal. When the symptom (discomfort) information is generated during the electrocardiogram signal is measured, the symptom (discomfort) information may be included in the electrocardiogram signal. When conducting the medical questionnaire, the medical may naturally refer to the past electrocardiogram analysis information and/or other medical history of the patient.

The analysis output controller 144a may generate and transmit electrocardiogram output data displaying the electrocardiogram signal and the classification data of the electrocardiogram signal to an external terminal.

Before the analysis condition is given, the analysis condition may be input based on an input interface of the analysis condition included in the electrocardiogram output data according to the control of the analysis output controller 144a. The analysis output controller 144a may generate the electrocardiogram output data displaying past data of an object, such as past medical history, current medical questionnaire items, questionnaire result, unusual matters regarding the previously measured electrocardiogram signal, etc. The analysis output controller 144a may determine one or more labels related to the past medical history, and/or current medical questionnaire items, etc. of the object by using a table showing a relation between medical history and labels and generate the electrocardiogram output data displaying the medical history, and/or current medical questionnaire items, etc.

Moreover, the analysis output controller 144a may generate output data regarding the sections of the electrocardiogram signal, which searches and displays the sections of the electrocardiogram signal with respect to the label related to the past medical history, medical questionnaire items, etc.

In this specification, the table showing a relation between the past medical history and/or medical questionnaire items may be stored in the electrocardiogram data processing server 100 or received from an external device through a network. The table showing a relation between the medical history and/or medical questionnaire items and the label may be modified by an input electrocardiogram signal, medical history information and/or (current or past) medical questionnaire items, etc. of an object. The table showing a relation between the medical history (kinds of disease, time of occurrence, etc.) and/or (current or past) medical questionnaire items may be modified by an expert. Data about labels related to age, gender, dwelling, occupation, race, smoking status, alcohol use, etc. of an object may be generated and managed.

The electrocardiogram output data may list the electrocardiogram signal per label and display the same. For example, the electrocardiogram output data may provide sections of the electrocardiogram signal classified into a first label, a second label, a third label, etc. The sections classified as the first label, the sections classified as the second label, and the sections classified as the third label may be displayed all at once.

The electrocardiogram output data may include data listed according to the priorities. The analysis output controller 144a may determine a priority among labels based on the information regarding the measured object, and the section data of each label may be displayed according to the priority. For example, the analysis output controller 144a may generate output data providing labels which require a detailed analysis according to past medical history, current medical questionnaire result, use of alcohol, smoking status, gender, age, etc. with respect to the sections corresponding to the labels. Moreover, the analysis output controller 144a may set a priority in relation to labels or sections according to past medical history, medical questionnaire result, use of alcohol, smoking status, gender, age, etc., determine labels having priority, and generate section data of each label based on the sections and labels. For example, when a first user has medical history showing slow pulse followed by unusual signal, output data separately providing labels and/or sections related to the slow pulse may be generated. Based on symptom (discomfort) sensing information experience by a second user, output data providing signal sections corresponding to the symptom (discomfort) sensing information and labels of the signal section may be generated. The analysis output controller 144a may generate output data displaying all at once labels classified by symptom and signal sections corresponding to the labels. The analysis output controller 144a may generate output data displaying all at once labels classified by symptom, regardless of time, and signal sections corresponding to the labels. The analysis output controller 144a may generate output data filtering the electrocardiogram signal by duration, occurrence period, occurrence time section, etc. For example, the analysis output controller 144a may generate output data displaying signal sections for labels maintained over 30 seconds; however, the disclosure is not limited thereto, and the analysis output controller 144a may filter the signal sections for the labels having duration input by the user. The analysis output controller 144a may generate output data displaying signal sections for labels occurred more than 10 times a day; however, the disclosure is not limited thereto, and the analysis output controller 144a may filter the signal sections for the labels having occurrence frequency input by the user. Moreover, the output data may be displayed on a daily basis (24 hours) or displayed after being analyzed by a particular time period.

The medical staff terminal 21 may access the electrocardiogram data processing server 100, receive the electrocardiogram output data including the electrocardiogram signal and the classification data of the electrocardiogram signal, and input the analysis condition corresponding to the classification data of the electrocardiogram signal. At least one of a label set, time, disease, illness, etc. may be set as the analysis condition. The analysis condition may include one or more labels, for example, the first label and the second label.

The feedback processor 145a may generate output data regarding a screen analyzing the electrocardiogram signal in response to the analysis request signal. The feedback processor 145a may transmit the output data to a designated analyst terminal.

The output data regarding the screen analyzing the electrocardiogram signal may include analysis target sections set with respect to the electrocardiogram signal and input comments about the analysis target sections. Furthermore, the output data may include a transmission-related area which facilitates transmission of comments, questions to the medical staff.

The feedback processor 145a may transmit the comments input by the analyst to the medical staff terminal and a response thereto to the analyst terminal. The feedback processor 145a may transmit the comments of the medical staff to the analyst terminal. The comments of the analyst and medical staff may be stored in association with the corresponding electrocardiogram signal.

The feedback processor 145a may generate data regenerated with various options of electrocardiogram signal and classification data thereof and transmit an analysis request signal therefor. The feedback processor 145a may generate data, excluding unusual signal sections of the signal according to an option of excluding duration of unusual signals and transmit an analysis request signal therefor. The feedback processor 145a may generate data of signal sections corresponding to labels having high weight, according to an option of applying a weight per label and transmit an analysis request signal therefor.

The feedback processor 145a may generate data of signal sections corresponding to the analysis condition or the option and transmit an analysis request signal therefor to the analyst terminal. The analyst terminal may be determined by the medical staff terminal or by the analyst terminal or by a task-assigning algorithm.

The feedback processor 145a may recommend an analyst terminal suitable for the analysis request signal. The feedback processor 145a may determine a proper analyst terminal considering the signal sections, labels, past medical history of an object, medical questionnaire items, etc. included in the analysis request signal. A proper analyst terminal may be determined based on performance histories of one or more analysts. The feedback processor 145a may determine as a proper analyst an analyst having analysis experience with respect to the labels of the signal sections or an analyst having analysis experience with respect to the signal sections corresponding to the past medical history and/or medical questionnaire items of an object.

The feedback processor 145a may receive an analysis report corresponding to the analysis request signal. The feedback processor 145a may perform the function of transmitting a reminder for the analysis report. When the analysis report is received, the feedback processor 145a may transmit an alarm therefor to the medical staff terminal.

The electrocardiogram data processing server 100 may store and manage the electrocardiogram signal, the classification data of the electrocardiogram signal, the analysis condition input with respect to the electrocardiogram signal, the expected analysis time of the electrocardiogram signal, the analysis report regarding the electrocardiogram signal, the feedback data additionally input with respect to the electrocardiogram signal, etc. The electrocardiogram data processing server 100 may manage stored data through an internal medium or an external electronic device.

In another embodiment, the analysis output controller 144a may display a first window displaying the analysis data of the electrocardiogram signal and a second window displaying the expected analysis time. The electrocardiogram signal or the analysis data of the electrocardiogram signal may be included in the first window of day or 24 hours unit. The expected analysis time may be classified and included in the second window per day. The analysis output controller 144a may calculate the expected analysis time by using the analysis data of the electrocardiogram signals performed previously and the classification data of the electrocardiogram signal. The analysis output controller 144a may generate data regarding the analysis times of the electrocardiogram signals previously performed by a plurality of analysts or a plurality of analysis modules registered with the server. The analysis output controller 144a may process a window displaying analysis processed data corresponding the data to be displayed on the user terminal. When an input to select an analyst is obtained by a user, the analysis output controller 144a may control the second window to display the expected analysis time for the case where the analysis of the electrocardiogram signal is performed by the selected analyst.

The analysis output controller 144a may calculate at least one of duration, symptom value, and label value of each signal section, and set, among the calculated information, first information as display set information and the rest of the information as hidden set information. The analysis output controller 144a may generate output data to classify the electrocardiogram signals as the first information, which is display set information, and output the same. The first information may be classified based on a measurement day.

The analysis output controller 144a may display a plurality of duration values, unusual symptoms, reference waveforms, etc. with respect to the electrocardiogram signals on a list screen and when an input to select a first value among the plurality of duration values, unusual symptoms, and reference waveforms is detected, the processor 120 may set the first value as the display set information. The analysis output controller 144a may process the signal sections corresponding to the first value to be displayed all at once in the user terminal. When a report signal for the analysis request signal is received, the analysis output controller 144a may transmit, to the medical staff terminal, output data according to the report signal, and when a confirm signal for the output data is received from the medical staff terminal, a state of the analysis request signal may be changed to a complete state.

Figure 5:
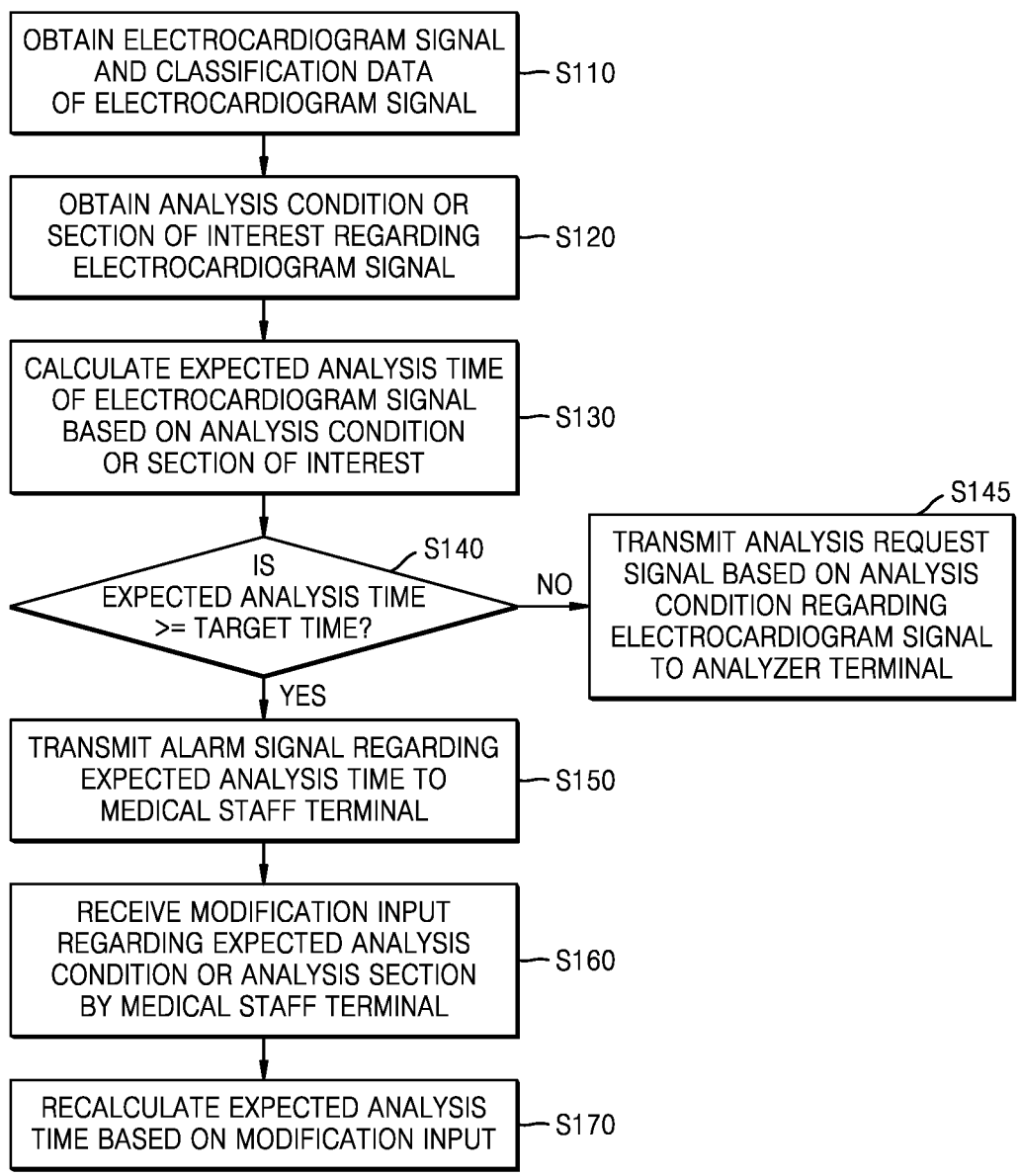
FIG. 5 is a flowchart of a method of processing electrocardiogram data according to one or more embodiments.

FIG. 5 is a flowchart of a method of processing electrocardiogram data according to embodiments.

In operation S110, the electrocardiogram data processing server 100 may obtain the electrocardiogram signal and the classification data of the electrocardiogram signal. The electrocardiogram signal may be measured for a certain period, for example, for 2 days or 14 days. The classification data of the electrocardiogram signal may include a category value time-sequentially displaying signal waveforms of the electrocardiogram signal and corresponding to each signal waveform. The category value may be a value converted into a label. The electrocardiogram data processing server 100 may divide the electrocardiogram signal into signal segments by a signal waveform, and set each signal segment as one of category values to generate the classification data of the electrocardiogram signal.

In operation S120, the electrocardiogram data processing server 100 may obtain the analysis condition or section of interest of the electrocardiogram signal. The analysis condition may be modified by the medical staff terminal. The electrocardiogram data processing server 100 may transmit the electrocardiogram output data displaying the electrocardiogram signal and the classification data of the electrocardiogram signal to the medical staff terminal. The analysis condition may be given with respect to the displayed electrocardiogram output data by the control of the medical staff terminal. The analysis condition may include a label value or time value. For initial iteration, the analysis condition may use a default value or a previous set value of the patient. Moreover, the analysis condition may use a set value recommended by artificial intelligence. The setting of the analysis condition may be performed by the medical staff in advance or interactively. In operation S120, the analysis condition to designating the entire section of the electrocardiogram signal may be obtained.

The section of interest may be determined by using the classification data of the electrocardiogram signal, sensing information included in bio-information, which is additionally input, or past medical history and/or medical questionnaire result of an object. The section of interest may be determined based on the analysis condition. The additionally input bio-information may include bio-information measured along with the electrocardiogram signal. The bio-information may include body temperature, blood glucose, blood pressure, respiration value, etc.

In operation S130, the electrocardiogram data processing server 100 may calculate the expected analysis time of the electrocardiogram signal based on the analysis condition. The electrocardiogram data processing server 100 may calculate an analysis time for each section of the electrocardiogram signal. The electrocardiogram data processing server 100 may calculate the expected analysis time of the electrocardiogram signal based on the analysis times of each section. The electrocardiogram data processing server 100 may extract the sections corresponding to the analysis condition and calculate the expected analysis time of the sections. The electrocardiogram data processing server 100 may calculate the expected analysis time considering the occurrence pattern of the sections, analysis time of the sections, noise occurrence pattern in the sections, etc.

When the expected analysis time is longer than a preset target time in operation S140, the electrocardiogram data processing server 100 may transmit an alarm signal for the expected analysis time to the medical staff terminal (S150). When the expected analysis time is less than the preset target time, the electrocardiogram data processing server 100 may transmit an analysis request signal for the electrocardiogram signal based on the analysis condition to the analyst terminal (S145). When the expected analysis time is less than the preset target time, the electrocardiogram data processing server 100 may transmit an alarm signal for the expected analysis time to the medical staff terminal.

In operation S160, the electrocardiogram data processing server 100 may receive, from the medical staff terminal, an analysis condition or a modification input for the analysis condition.

In operation S170, the electrocardiogram data processing server 100 may recalculate the expected analysis time based on the modification input. When the modification input is an input to modify the analysis condition or the analysis section, the electrocardiogram data processing server 100 may obtain again, in response to the modification input, the analysis target signal to be analyzed in correspondence with the analysis condition or the analysis section and recalculate the noise duration and the ratio of the noise duration with respect to the analysis target signal.

When the modification input is given to modify the target time, the electrocardiogram data processing server 100 may generate output data with a modified target time in response to the modification input. The analysis request signal for the electrocardiogram signal may be generated based on the modified target time.

Figure 6:
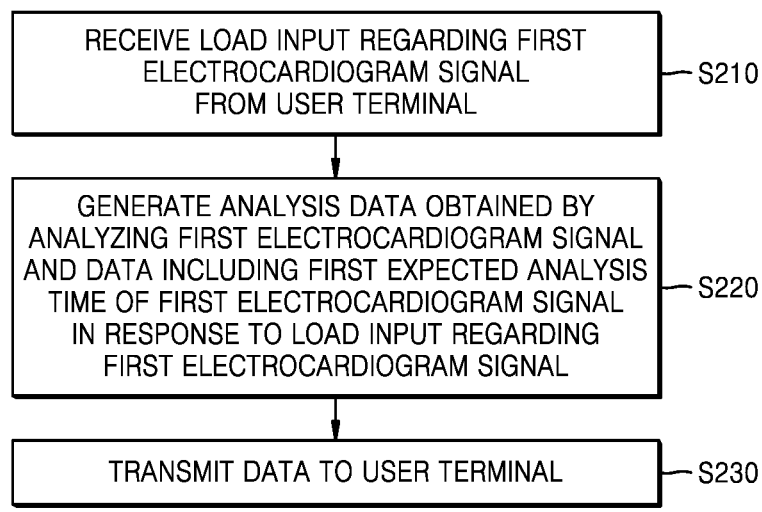
FIG. 6 is a flowchart of a method of transmitting data to a user device and displaying the same according to one or more embodiments.

FIG. 6 is a flowchart of a method of transmitting data to a user device and displaying the same according to embodiments.

In operation S210, the electrocardiogram data processing server 100 may receive a load input for a first electrocardiogram signal from the user terminal.

In operation S220, the electrocardiogram data processing server 100 may generate, in response to the load input for the first electrocardiogram signal, data including the first electrocardiogram signal and a first expected analysis time of the first electrocardiogram signal to the user terminal.

In operation S230, the electrocardiogram data processing server 100 may transmit the data to the user terminal. The electrocardiogram data processing server 100 may generate output data including a first window displaying the analysis data of the first electrocardiogram signal and a second window displaying the first expected analysis time. The electrocardiogram signal or the analysis data of the electrocardiogram signal may be included in the first window of day or 24 hours unit. The expected analysis time may be classified and included in the second window per day.

Figure 7:
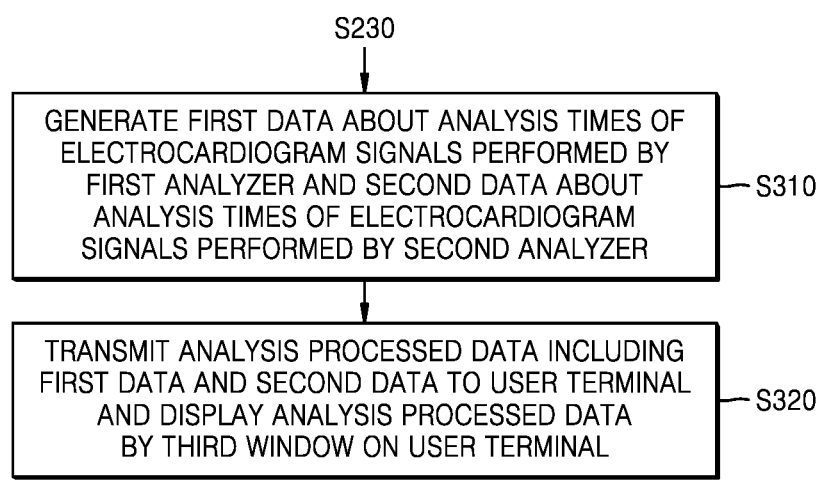
FIG. 7 is a flowchart of a method of displaying data regarding expected analysis times for an analyst according to one or more embodiments.

FIG. 7 is a flowchart of a method of displaying data regarding expected analysis times for an analyst according to embodiments.

In operation S310, the electrocardiogram data processing server 100 may generate first data about analysis times of the electrocardiogram signals performed by the first analyst and second data about analysis times of the electrocardiogram signals performed by the second analyst. The electrocardiogram data processing server 100 may classify the first data analyzed by the first analyst and the second data analyzed by the second analyst, respectively, from among the analysis data analyzed in the past. The first and second data may be interchangeable with the analysis data.

In operation S320, the electrocardiogram data processing server 100 may transmit analysis processed data including the first data and the second data to the user terminal. A third window displaying the analysis processed data may be displayed on the user terminal.

Figure 8:
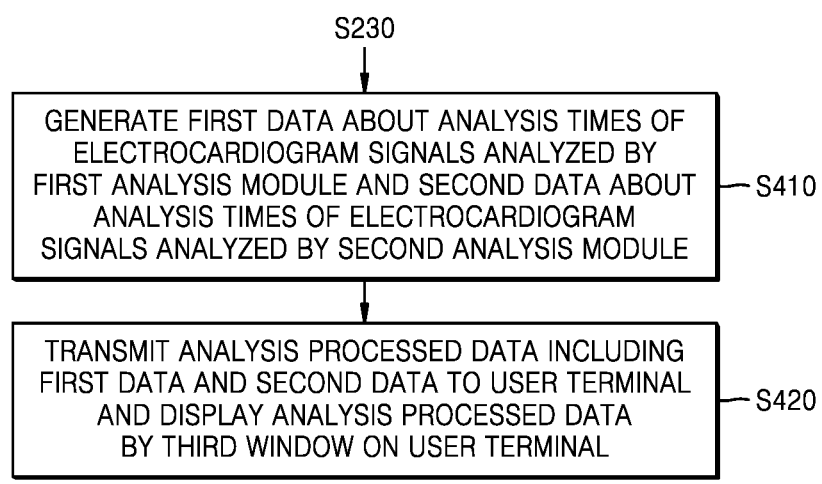
FIG. 8 is a flowchart of a method of displaying data regarding expected analysis times for an analyst according to one or more embodiments.

FIG. 8 is a flowchart of a method of displaying data regarding expected analysis times for an analyst according to embodiments.

In operation S410, the electrocardiogram data processing server 100 may generate first data about analysis times of the electrocardiogram signals analyzed by the first analysis module and second data about analysis times of the electrocardiogram signals analyzed by the second analysis module.

In operation S420, the electrocardiogram data processing server 100 may transmit analysis processed data including the first data and the second data to the user terminal. A third window displaying the analysis processed data may be displayed on the user terminal.

Figure 9:
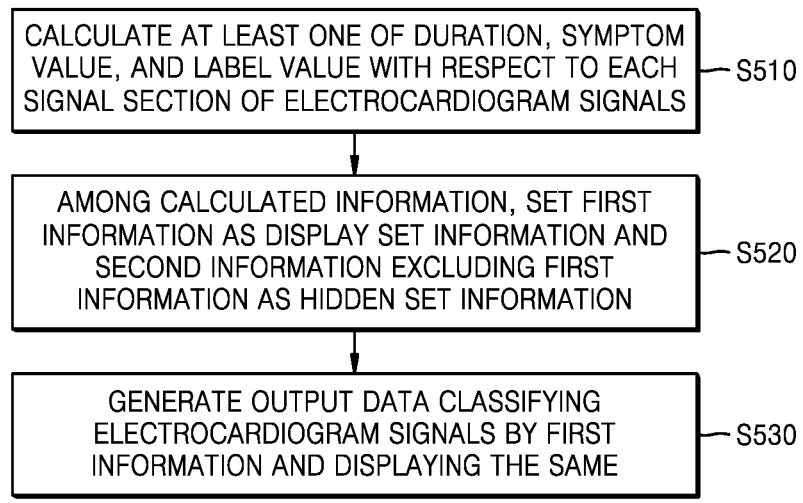
FIG. 9 is a flowchart of method of reclassifying information into display set information regarding an electrocardiogram signal according to one or more embodiments.

FIG. 9 is a flowchart of method of reclassifying information into display set information regarding an electrocardiogram signal according to embodiments.

In operation S510, the electrocardiogram data processing server 100 may calculate at least one of duration, symptom value, and label value with respect to each signal section of the electrocardiogram signals.

In operation S520, the electrocardiogram data processing server 100 may set first information from the calculated information as display set information and second information excluding the first information as hidden set information. The first information may be classified based on a measurement day.

In operation S530, the electrocardiogram data processing server 100 may generate output data classifying the electrocardiogram signals by the first information and displaying the same.

The electrocardiogram data processing server 100 may display a plurality of duration values, symptom values, unusual symptoms, reference waveforms on the list screen from the user terminal.

The electrocardiogram data processing server 100 may generate output data setting a first duration value, a first symptom value, a first unusual symptom, and a first reference waveform selected by the user as display set information, searching signal sections corresponding to one of the first duration value, the first symptom value, the first unusual symptom, and the first reference waveform, displaying searched signal sections, and displaying the rest of the signal sections as hidden set information.

When the input complete signal for the output data is detected, the electrocardiogram data processing server 100 may generate an analysis request signal for the signal sections of the electrocardiogram signal included in the output data and transmit the analysis request signal to the analyst terminal.

As analyzing the entire electrocardiogram signal may take a long time, the electrocardiogram data processing server 100 may request an analysis of a part of the electrocardiogram signal to reduce the analysis time. When a select input with respect to at least one of duration, symptom value, unusual symptom, and reference waveform is received from the medical staff terminal, output data displaying aggregated signal sections corresponding to the select input may be generated. The electrocardiogram data processing server 100 may display the output data on the user terminal.

Figure 10:
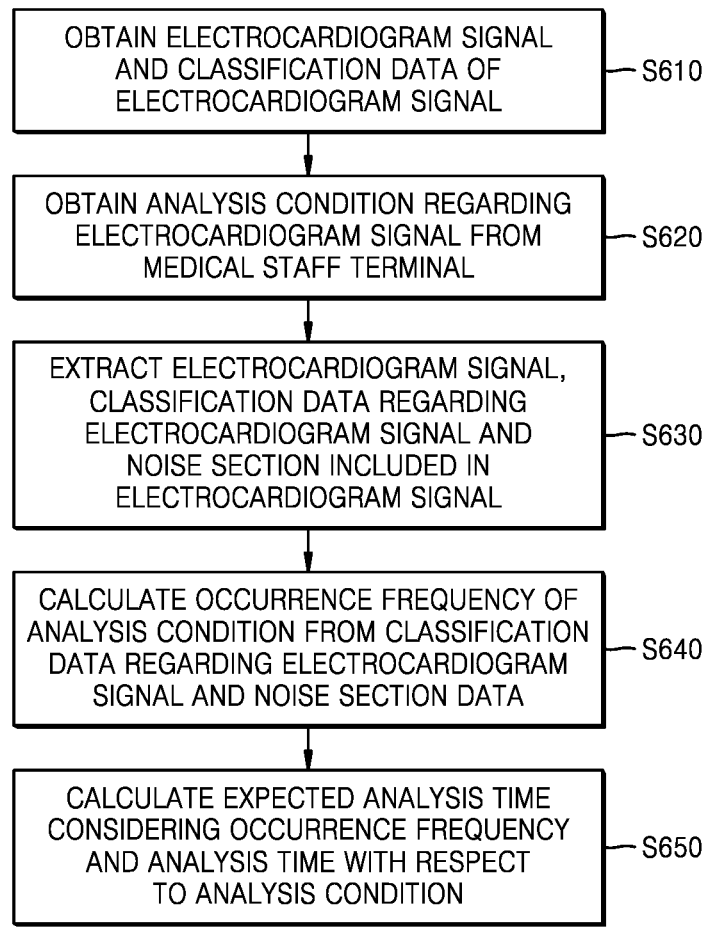
FIG. 10 is a flowchart of a method of calculating expected analysis time according to one or more embodiments.

FIG. 10 is a flowchart of a method of calculating expected analysis time according to embodiments.

In operation S610, the electrocardiogram data processing server 100 may obtain the electrocardiogram signal and the classification data of the electrocardiogram signal.

In operation S620, the electrocardiogram data processing server 100 may obtain the analysis condition of the electrocardiogram signal from the medical staff terminal.

In operation S630, the electrocardiogram data processing server 100 may extract data regarding the noise section in the section corresponding to the electrocardiogram signal, the classification data of the electrocardiogram signal, and the analysis condition. The electrocardiogram data processing server 100 may separately calculate the analysis time of the noise section.

In operation S640, the electrocardiogram data processing server 100 may calculate the occurrence frequency of the analysis condition in the classification data of the electrocardiogram signal. The electrocardiogram data processing server 100 may calculate the occurrence frequency considering time of occurrence of the sections corresponding to the analysis condition.

In operation S650, the electrocardiogram data processing server 100 may calculate the expected analysis time considering the occurrence frequency and the analysis time under the analysis condition. The electrocardiogram data processing server 100 may calculate the first expected analysis time considering the occurrence frequency and analysis time of the section in correspondence with the analysis condition and modify the analysis time of the noise section to the first expected analysis time to calculate the expected analysis time. The expected analysis time may calculate a reference time based on the past performance of the analyst. An actual analysis time may vary according to analysts. Selection of analyst may be made considering differences among the analysts. The electrocardiogram data processing server 100 may render the entire or a part of analysis process to be performed by an analysis module implemented by artificial intelligence.

FIG. 11 is a flowchart of a method of calculating expected analysis time based on an analysis condition input as a label according to embodiments.

In operation S710, the electrocardiogram data processing server 100 may obtain the electrocardiogram signal and the classification data of the electrocardiogram signal.

In operation S720, the electrocardiogram data processing server 100 may generate output data displaying the classification data of the electrocardiogram signal.

In operation S730, the electrocardiogram data processing server 100 may transmit the output data to the medical staff terminal so that the electrocardiogram signal and the classification data of the electrocardiogram signal are displayed on the medical staff terminal. The output data may include the entire electrocardiogram signal data, noise duration value, and information regarding the entire monitoring time, and may also include daily noise duration value and daily monitoring time value. The electrocardiogram data processing server 100 may provide data analyzed by the classification condition after analyzing the electrocardiogram signal by the classification condition and selecting the noise and information about the noise, e.g., section, occurrence position, duration, etc. Furthermore, the output data may include information about a level of noise occurrence ratio, i.e., whether it is general, high or low.

In operation S740, the electrocardiogram data processing server 100 may receive the analysis condition including the first label and the second label selected by the medical staff terminal. The analysis condition may be determined among labels of the electrocardiogram signal included in the output data; however, the disclosure is not limited thereto, and the analysis condition may be selected from a list of labels included in the electrocardiogram signal.

In operation S750, when the analysis condition is received, the electrocardiogram data processing server 100 may calculate the expected analysis time based on the analysis condition and display the expected analysis time on the medical staff terminal. The electrocardiogram data processing server 100 may calculate noise duration among the parameters used for analysis time estimation. The electrocardiogram data processing server 100 may calculate the occurrence pattern of the noise based on the noise duration. The electrocardiogram data processing server 100 may calculate the occurrence pattern of the section corresponding to the first label and the second label of the electrocardiogram signal. The electrocardiogram data processing server 100 may calculate the first expected analysis time by multiplying the analysis time of the section corresponding to the first label and the second label by the occurrence pattern of the section, calculate the second expected analysis time considering the noise occurrence pattern in the electrocardiogram signal and the analysis time of the noise, and calculate a final expected analysis time by adding the first expected analysis time to the second expected analysis time.

Figure 12:
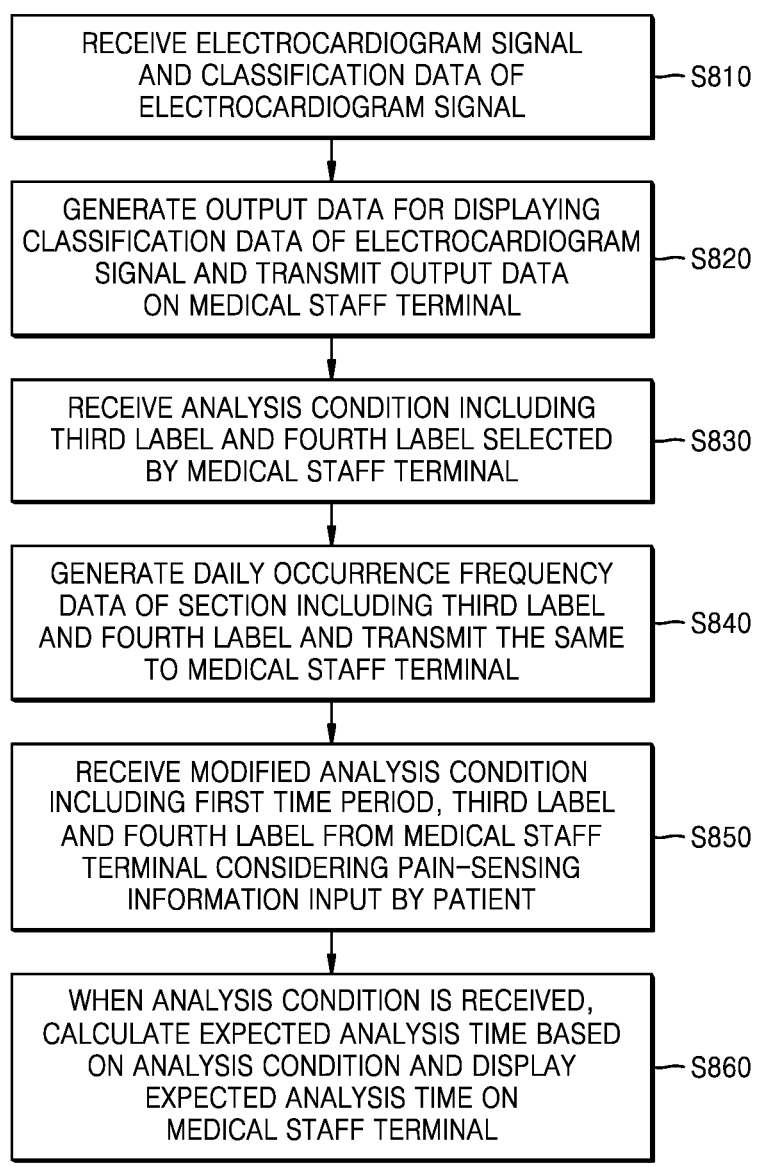
FIG. 12 is a flowchart of a method of regenerating and analyzing a modified condition based on symptom (discomfort) sensing information according to one or more embodiments.

FIG. 12 is a flowchart of a method of regenerating and analyzing a modified condition based on pain (discomfort) sensing information according to embodiments.

In operation S810, the electrocardiogram data processing server 100 may receive the electrocardiogram signal and the classification data of the electrocardiogram signal.

In operation S820, the electrocardiogram data processing server 100 may generate output data displaying the classification data of the electrocardiogram signal and transmit the output data to the medical staff terminal.

In operation S830, the electrocardiogram data processing server 100 may receive the analysis condition including the third label and the fourth label selected by the medical staff terminal.

In operation S840, the electrocardiogram data processing server 100 may generate daily occurrence frequency data regarding the section including the third label and the fourth label and transmit the same to the medical staff terminal.

In operation S850, the electrocardiogram data processing server 100 may receive a modified analysis condition including the first period, the third label, and the fourth label from the medical staff terminal considering the symptom (discomfort) sensing information input by the patient. The symptom (discomfort) sensing information may be information about the symptoms (discomfort) experienced by the patient during the electrocardiogram measurement, and may include time of sensing the symptom (discomfort), degree of the symptom (discomfort), details of the symptom (discomfort), etc. The symptom (discomfort) sensing information may be included in the electrocardiogram signal or obtained separately through communications with the patient (medical questionnaire, online consultation, etc.) The electrocardiogram data processing server 100 may modify the analysis condition based on the symptom (discomfort) sensing information. Moreover, the electrocardiogram data processing server 100 may check the symptom (discomfort) sensing information in the medical staff terminal and modify the analysis condition. The first period including the sensing time of the symptom (discomfort) may be included in the analysis condition by the electrocardiogram data processing server 100 so that the analysis is conducted focusing on the sensing time of the symptom (discomfort). The electrocardiogram data processing server 100 may receive an input in which the first period is included in the analysis condition from the medical staff terminal.

In operation S860, when the analysis condition is received, the electrocardiogram data processing server 100 may calculate the expected analysis time based on the analysis condition and display the expected analysis time on the medical staff terminal. The electrocardiogram data processing server 100 may extract sections including the third label and the fourth label from the data regarding the first period, which is the modified analysis condition to calculate the expected analysis time of the sections.

Figure 13:
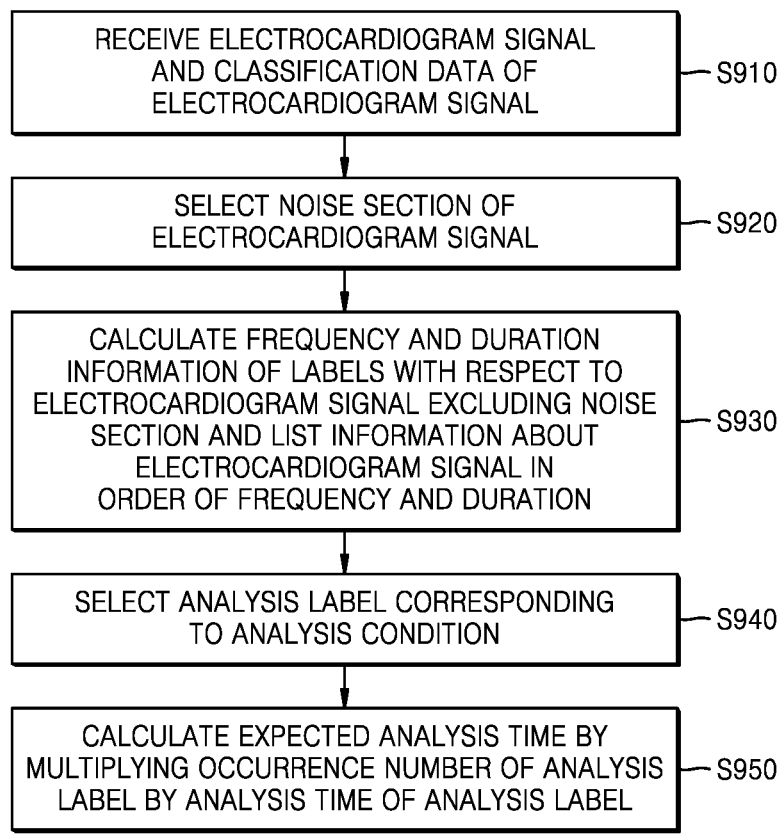
FIG. 13 is a flowchart of a method of analyzing electrocardiogram data according to one or more embodiments.

FIG. 13 is a flowchart of a method of analyzing electrocardiogram data according to embodiments.

In operation S910, the electrocardiogram data processing server 100 may receive the electrocardiogram signal and the classification data of the electrocardiogram signal.

In operation S920, the electrocardiogram data processing server 100 may select a noise section of the electrocardiogram signal.

In operation S930, the electrocardiogram data processing server 100 may calculate frequency of labels of the electrocardiogram signal excluding the noise section and duration information of the labels and list the information about the electrocardiogram signal according to the order determined based on the frequency and the duration. The output data implemented to list the section data of the electrocardiogram signal in an ascending order of frequency, descending order of frequency, ascending order of duration, and descending order of duration may be generated.

In operation S940, the electrocardiogram data processing server 100 may select an analysis label corresponding to the analysis condition.

In operation S950, the electrocardiogram data processing server 100 may calculate the expected analysis time by multiplying the occurrence number of the analysis label by the analysis time of the analysis label.

FIG. 14 is a diagram illustrating an example of a label included in classification data of an electrocardiogram signal according to an embodiment.

As illustrated in FIG. 14, the classification data of the electrocardiogram signal may include labels generated according to three steps. In the first step, the electrocardiogram signal may be classified by category values (labels) including a normal beat N, a supraventricular ectopy beat (SVEB) S, and ventricular ectopy beat V according to a certain classification criteria. The classification criteria may be in accordance with international standard IEC 60601-2-47 or domestic standard KS C IEC 60601-2-47, etc.; however, the disclosure is not limited thereto. Furthermore, the classification criteria may be modified or added by the user.

N, S, and V in the first step may each be classified by category values of the second step. The category value of N may be sub-classified by category values of C2-N. The category value of S may be sub-classified by category values of C2-S. The category value of V may be sub-classified by category values of C2-V.

According to an embodiment, the electrocardiogram signal may be classified based on the category values (C2-N, C2-S, and C2-V) and then classified by representative waveforms of each category. The electrocardiogram signal data stream may be classified by the category values and the representative signal waveform of each category on a signal segment basis. The category values may be designed to respectively correspond to the labels.

FIG. 15 is a diagram of analysis target sections satisfying an analysis condition.

When labels of a first label AFIB_1 and a second label AFIB_2 are input as the analysis condition by the medical staff, the electrocardiogram data processing server 100 may search sections corresponding to the first label AFIB_1 and sections corresponding to the second label AFIB_2 as well as occurrence date, occurrence staring time point, duration, occurrence termination time point, etc. with respect to the sections. The electrocardiogram data processing server 100 may tabulate and store the searched data as illustrated in FIG. 15. NSR-AF-PAUSE-NSR and NSR-AF-NSR are examples of the first label AFIB_1 and the second label AFIB_2, respectively.

Figure 16:
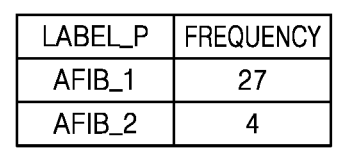
Figure 17:
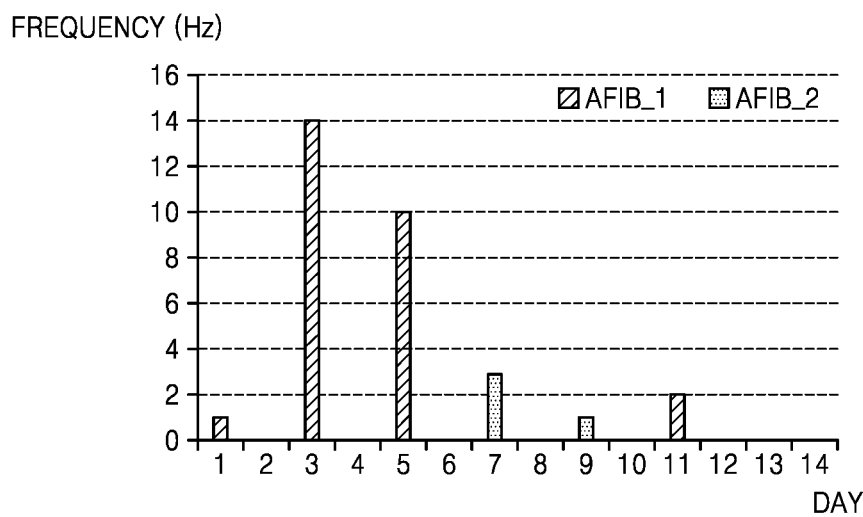
FIG. 17 is a graph showing daily occurrence frequency of the analysis target sections of FIG. 15.

FIG. 16 is a diagram showing an example of a frequency of occurrence of a first label and a second label in analysis target sections of FIG. 15, and FIG. 17 is a graph showing daily occurrence frequency of the analysis target sections of FIG. 15.

The electrocardiogram data processing server 100 may count and store occurrence frequency of sections corresponding to the first label AFIB_1 and the second label AFIB_2. The electrocardiogram data processing server 100 may count and store daily occurrence frequency of sections corresponding to the first label AFIB_1 and the second label AFIB_2. The electrocardiogram data processing server 100 may transmit the data about the occurrence frequency of the sections corresponding to the first label AFIB_1 and the second label AFIB_2 to the medical staff terminal so that the data about the occurrence frequency is displayed on the medical staff terminal.

As illustrated in FIG. 17, during the 14 days of measurement, the information showing that the first label AFIB_1 occurred 14 times in day 3 and 10 times in day 5 may be extracted. The information showing that the second label AFIB_2 occurred 3 times in day 7 may be extracted. The daily occurrence frequency during the measurement period may be tabulated. The first label AFIB_1 may be searched as being occurred most in day 3. The electrocardiogram data processing server 100 may store the data regarding the daily occurrence frequency. The electrocardiogram data processing server 100 may transmit the data about the daily occurrence frequency of the sections corresponding to the first label AFIB_1 and the second label AFIB_2 to the medical staff terminal so that the data about the daily occurrence frequency is displayed on the medical staff terminal.

Figure 18:
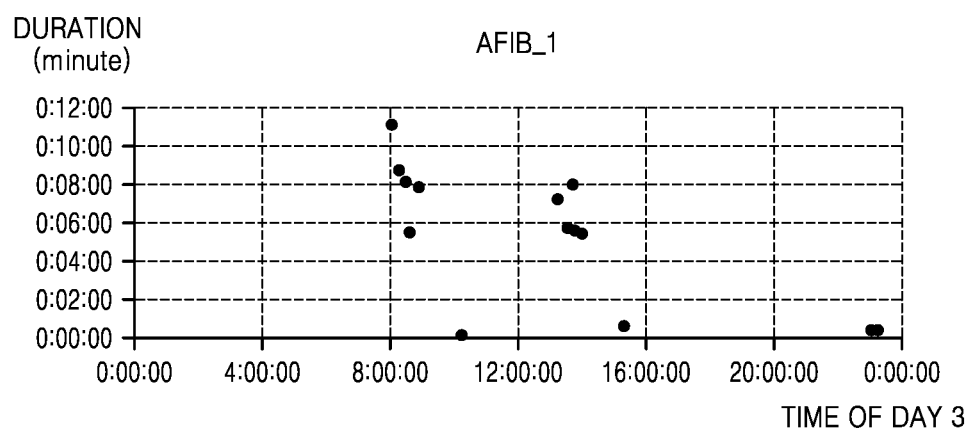
FIG. 18 is a graph showing a time point of occurrence of a first label of FIG. 16.

FIG. 18 is a graph showing a time point of occurrence of a first label AFIB_1 of FIG. 16.

The electrocardiogram data processing server 100 may generate and store a graph showing the relation between the occurrence time point and frequency. The electrocardiogram data processing server 100 may transmit the graph showing the relation between the occurrence time point and frequency to the medical staff terminal.

Figure 19A:
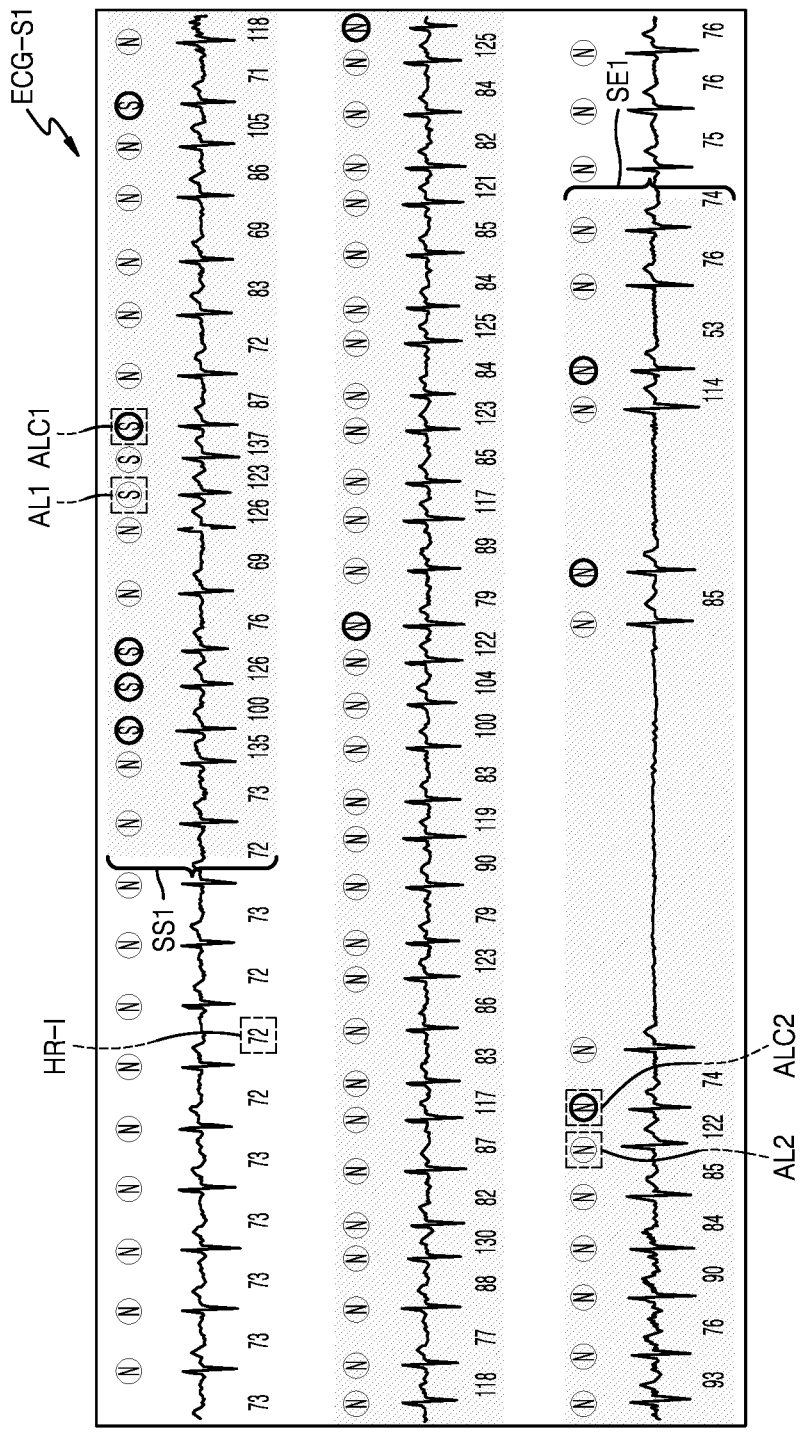
FIG. 19A is a diagram illustrating an example of first output data including a first electrocardiogram signal and labels.
Figure 19B:
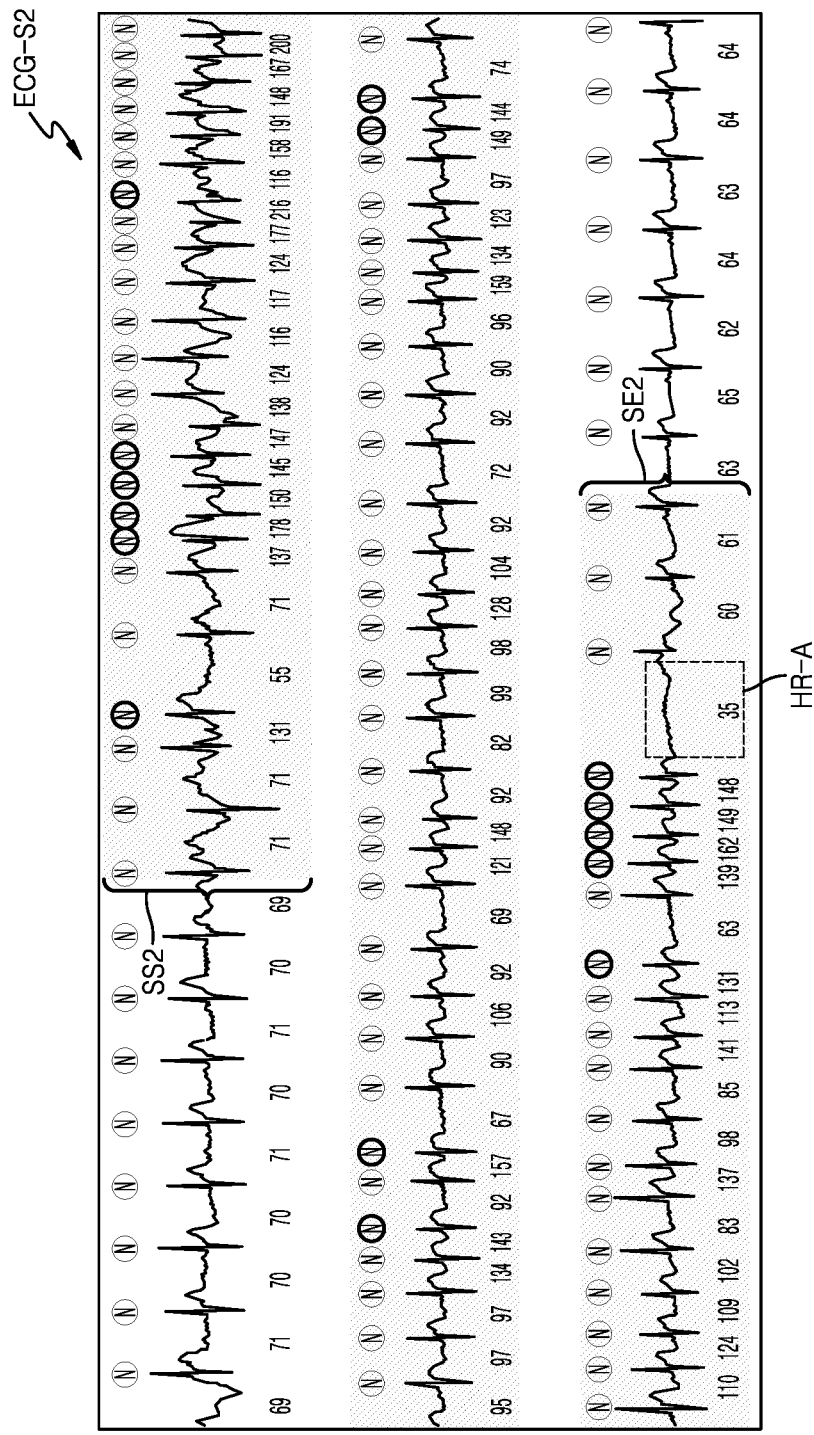
FIG. 19B is a diagram illustrating an example of second output data including a second electrocardiogram signal and heart rates.

FIG. 19A is a diagram illustrating an example of first output data including a first electrocardiogram signal and labels. FIG. 19B is a diagram illustrating an example of second output data including a second electrocardiogram signal and heart rates.

The electrocardiogram data processing server 100 may generate the output data regarding the electrocardiogram signal and the classification data of the electrocardiogram signal as illustrated in FIG. 19A.

A first signal section (SS1 to SE1) of FIG. 19A may have a waveform corresponding to the first label AFIB_1 and may be section in which the pulse rate starts out of the normal range, has fibrillation and then return to the normal range. The first section may include a section where heart rate=1 (PAUSE). The classification data ECG-S1 of the electrocardiogram signal may include a heart rate HR-1 and labels (AL1, ALC2, AL2, and ALC2) within a set time interval. The labels generated by an algorithm generating the classification data may be marked as AL1, AL2, etc. The labels modified by the analyst after they are generated may be marked as ALC1, ALC2, etc. That is, the labels generated by the algorithm and the labels modified by the analyst after generation may be displayed differently.

A second time section (SS2 to SE2) of FIG. 19B may be characterized by not including a section where heart rate=0 as a time section corresponding to the second label AFIB_2. As for HR-A included in the classification data ECG-S2 of the electrocardiogram signal illustrated in FIG. 19B, although there is a PAUSE label, as the heart rate is not 0, it is not deemed as PAUSE.

The device described above may be implemented by a hardware component, a software component, and/or combination of a hardware component and a software component. For example, the device and components described in the embodiments may be implemented by using one or more general purpose computers or special purpose computers such as a processor, a controller, an arithmetic logic unit (ALU), a DSP, a microcomputer, an FPGA, a programmable logic unit (PLU), a microprocessor, or any other devices capable of executing and responding to instructions. A processing unit may be executing an operating system and one or more software applications run in the operating system. Moreover, the processing unit may access, store, manipulate, process, and generate data in response to execution of software. For convenience in understanding, some embodiments describe that one processing unit is used; however, a person skilled in the art may understand that the processing unit may include a plurality of processing elements and/or various types of processing elements. For example, the processing unit may include a plurality of processors or one processor and one controller. Other processing configurations including a parallel processor, etc. may also be possible.

The software may include a computer program, a code, and instruction, or a combination of one or more of the foregoing, and may configure the processing unit to operate in a desired manner or command independently or collectively the processing unit. The software and/or data may be embodied permanently or temporarily in a certain type of machine, a component, a physical device, a virtual equipment, a computer storage medium or device, or a signal wave to be transmitted to be interpreted by the processing unit or provide instruction or data to the processing unit. The software may be dispersed in a computer system connected by a network and be stored or executed in dispersed manner. The software of data may be stored in one or more computer-readable recording media.

The method according to embodiments may be implemented in the form of a program instruction executable by various computing devices and recorded in a computer-readable medium. The computer-readable medium may include a program instruction, a data file, a data structure, etc. separately or combinedly. The program instruction recorded to the medium may be specifically designed and configured for embodiments or may be made public and usable to a person skilled in the field of computer software. The computer-readable recording medium may include a hardware device specifically configured to store and execute program instructions, such as magnetic media including a hard disk, a floppy disk, and a magnetic tape, optical media such as a CD-ROM and a DVD, magneto-optical media such as a floptical disk, ROM, RAM, flash memory, etc. The program instructions may include not only machine language code, which is made by a compiler, but high level language code executable by a computer by using an interpreter, etc. The hardware device may be configured to operate by one or more software modules to perform operations of embodiments, and vice versa.

In the embodiments, the output data calculating at least one of duration, symptom value, and label value with respect to each signal section, setting first information of the calculated information as display set information, second information excluding the first information as hidden set information, classifying the electrocardiogram signals by the first information and displaying the classification result may be generated.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A method of displaying analysis data of an electrocardiogram signal, the method comprising:
   calculating, by an electrocardiogram data processing server, information including at least one of a duration, a symptom value, and a label value with respect to each signal section of electrocardiogram signals;
   among calculated information, setting, by the electrocardiogram data processing server, first information as display set information and second information excluding the first information as hidden set information;
   generating, by the electrocardiogram data processing server, output data for classifying the electrocardiogram signals by the first information for display;
   generating, by the electrocardiogram data processing server, an analysis request signal for signal sections of the electrocardiogram signals included in the output data in response to an input completion signal for the output data; and
   transmitting, by the electrocardiogram data processing server, the analysis request signal to an analyst terminal, wherein setting of the first information and the second information further comprises displaying a plurality of symptom values which are set with respect to the electrocardiogram signals on a list screen of the analyst terminal, and
   in response to an input to select a first symptom value among the plurality of symptom values, setting the first symptom value as display set information and a rest of information as the hidden set information.

2. The method of claim 1, wherein setting of the first information and the second information further comprises displaying, by the electrocardiogram data processing server, a plurality of duration values which are set with respect to the electrocardiogram signals on a list screen of the analyst terminal, and
   when an input to select a first duration value among the plurality of duration values is detected, setting the first duration value as display set information and the rest of information as the hidden set information.

3. A method of displaying analysis data of an electrocardiogram signal, the method comprising:
   calculating, by an electrocardiogram data processing server, information including at least one of a duration, a symptom value, and a label value with respect to each signal section of electrocardiogram signals;
   among calculated information, setting, by the electrocardiogram data processing server, first information as display set information and second information excluding the first information as hidden set information;
   generating, by the electrocardiogram data processing server, output data for classifying the electrocardiogram signals by the first information for display;
   generating, by the electrocardiogram data processing server, an analysis request signal for signal sections of the electrocardiogram signals included in the output data in response to an input completion signal for the output data; and
   transmitting, by the electrocardiogram data processing server, the analysis request signal to an analyst terminal,
   wherein setting of the first information and the second information further comprises displaying a plurality of unusual symptoms set with respect to the electrocardiogram signals on a list screen of the analyst terminal, and
   in response to an input to select a first unusual symptom among the plurality of unusual symptoms, setting the first unusual symptom as display set information and a rest of information as the hidden set information.

4. The method of claim 3, wherein the setting of the first information and the second information comprises displaying a plurality of reference waveforms which are set with respect to the electrocardiogram signals on a list screen, and
   in response to an input to select a first reference waveform among the plurality of reference waveforms, setting the first reference waveform as display set information and the rest of information as the hidden set information.

5. The method of claim 3, further comprising:
   generating an analysis request signal for signal sections of an electrocardiogram signal included in the output data when an input complete signal for the output data is detected, and transmitting the analysis request signal to the analyst terminal.

6. The method of claim 3, further comprising:
   in response to a report signal for the analysis request signal, transmitting, by the electrocardiogram data processing server, output data according to the report signal to a medical staff terminal; and
   in response to a confirm signal for the output data from the medical staff terminal, changing, by the electrocardiogram data processing server, a status of the analysis request signal to a complete status.

7. The method of claim 3, wherein the first information or the second information includes data classified on a measurement day basis for display.

\* \* \* \* \*